(12) United States Patent
Seiki et al.

(10) Patent No.: US 6,184,022 B1
(45) Date of Patent: Feb. 6, 2001

(54) METALLOPROTEINASE AND ENCODING DNA THEREFOR

(75) Inventors: Motoharu Seiki; Hiroshi Sato, both of Kanazawa; Akira Shinagawa, Takaoka, all of (JP)

(73) Assignee: Fuji Yakuhin Kogyo Kabushiki Kaisha, Toyama-ken (JP)

( * ) Notice: Under 35 U.S.C. 154(b), the term of this patent shall be extended for 0 days.

(21) Appl. No.: 08/448,489

(22) Filed: Jun. 7, 1995

Related U.S. Application Data

(63) Continuation-in-part of application No. PCT/JP94/02009, filed on Nov. 30, 1994.

(30) Foreign Application Priority Data

Nov. 30, 1993 (JP) .................................... 5-341061
Mar. 31, 1995 (JP) .................................... 7-109884

(51) Int. Cl.⁷ .............................. C12N 9/64; C12N 15/57
(52) U.S. Cl. ........................................ 435/226; 536/23.2
(58) Field of Search ............................ 435/226; 536/23.2

(56) References Cited

U.S. PATENT DOCUMENTS

| | | | |
|---|---|---|---|
| 5,236,844 | 8/1993 | Basset et al. | 435/320.1 |
| 5,484,726 | 1/1996 | Basset et al. | 435/7.4 |

FOREIGN PATENT DOCUMENTS

| | | |
|---|---|---|
| 9209701 | 6/1992 | (WO) . |
| WO9525171A2 | 9/1995 | (WO) . |

OTHER PUBLICATIONS

PCR Technology, Stockton Press, pp. 63–67 (1989).
Okada et al., *Proc. Natl. Acad. Sci.*, USA, vol 92, pp. 2730–2734 (Mar. 1995).
Sato et al., Nature, 370, 61–65 (1994).
Pajouh et al., J. Cancer Res. Clin. Oncol. 117:144–150 (1991).
Liotta, Cancer Research, 46, 1–7 (1986).
Ballin et al., Biochem. Biophys. Res. Commun., 154, 832–838 (1988).
Aznavoorian et al., Cancer, 71, 1368–1383 (1993).
Ogata et al., J. Biol. Chem., 267, 3581–3584 (1992).
Kohler et al., Nature, 256, 495–497 (1975).
Chirgwin et al., Biochemistry, 18, 5294–5299 (1979).
Gubler et al., Gene, 25, 263–269 (1983).
Molecular Cloning, A Laboratory Manual, 2.78 (1989) Sambrook et al., Cold Spring Harbor Labs.
Kyte et al., J. Mol. Biol., 157, 105–132 (1982).
Selected Methods in Cellular Immunology, 351–372 (1980) Oi et al. W.H. Freeman & Co., San Francisco.
Zhang et al., Clin. Chim. Acta, 219, 1–14 (1993).
Fujimoto et al., Clin. Chem. Acta, 221, 91–103 (1993).
Obata et al., Clin. Chim. Acta, 211, 59–72 (1992).
Miyazaki et al., Cancer Research 50, 7758–7764 (1990).
Knauper et al., Biol. Chem. Hoppe–Seyler, 371, 295–304 (1990).
Okada et al., J. Biol. Chem. 267, 21712–21719 (1992).
Strongin et al., J. Biol. Chem., 268, 14033–14039 (1993).
Albini et al., Cancer Research, 47, 3239–3245 (1987).
A.Y. Strongin et al. "Mechinism of Cell Surface Activation of 72–kDa Type IV Collagenase", J. Biol. Chem. 270(10):5331–5338, Mar. 1995.*

* cited by examiner

*Primary Examiner*—Rebecca Prouty
(74) *Attorney, Agent, or Firm*—Birch, Stewart, Kolasch & Birch, LLP.

(57) ABSTRACT

A novel metalloproteinase, DNA encoding therefor, a plasmid carrying said DNA sequence and a host cell harbouring said plasmid, and monoclonal antibodies peculiarly recognizing said protein.

Useful in applications pertaining to diagnosis of the presence of tumour cells, the degree of cancer malignancy, and other medical and physiological fields.

5 Claims, 15 Drawing Sheets

Fig. 2A

|  |  |  |  |  |  |
|---|---|---|---|---|---|
| MMP-11 | MAPAAWLRSA | AARALLPPML | LLLLQPPPL- | ---------- | ----LARA | 33 |
| MMP-1 | MHS------- | ---------- | -FPPL | LLLLFWGVVS | HSFPATLETQ | EQDVDLVQKY | 37 |
| MMP-8 | MFSLKTL--- | ---------- | -PFL | LLLHVQISKA | FPVSSKEKNT | KTVQD----Y | 36 |
| MMP-10 | MMHL------ | ---------- | -AFL | VLLCLPVCSA | YPLSGAAKEE | DSNKDLAQQY | 37 |
| MMP-3 | MKSL------ | ---------- | -PIL | LLLCVAVCSA | YPLDGAARGE | DTSMNLVQKY | 37 |
| MMP-9 | MSLWQP---- | ---------- | -LVIVLLIV | LGCCFAAPRQ | RQSTLVLFPG | DLRTNLTDRQ | 43 |
| MMP-2 | ---------- | ---------- | -AP-- | ---------- | --SPIIKFPG | DVAPK-TDKE | 19 |
| MMP-7 | MR-------- | ---------- | ---------- | CLIPGSLALP | LPQEAGGMSE | ----LQWE | 33 |
| MT-MMP | MSPAP----- | ---------- | -LTVLCAV | CLLLPLLTLG | TALASLGSAQ | SSSFS-PEAW | 38 |

Consensus | M......... | ---------- | ....P.L | LLL....... | .......... | .......... | 50

|  |  |  |  |  |  |
|---|---|---|---|---|---|
| MMP-11 | LPPDVHHL-- | ---HAERR-G | PQPWHAALPS | SP---APAPA | TQEAPRPASS | 74 |
| MMP-1 | L-EKYYNLKN | DGRQVEKRRN | SGPVVEKLKQ | MQEFFGLKVT | GKPDAETLKV | 86 |
| MMP-8 | L-EKFYQLPS | NQYQSTRKNG | TNVIVEKLKE | MQRFFGLNVT | GKPNEETLDM | 85 |
| MMP-10 | L-EKYYNLEK | DVKQFRRK-D | SNLIVKKIQG | MQKFLGLEVT | GKLDTDTLEV | 85 |
| MMP-3 | L-ENYYDLKK | DVKQFVRRKD | SGPVVKKIRE | MQKFLGLEVT | GKLDSDTLEV | 86 |
| MMP-9 | LAEEYLYRYG | YTRVAEMRGE | SKSLGPALLL | LQKQLSLPET | GELDSATLKA | 93 |
| MMP-2 | LAVQYLNTF- | YGCPKE-SCN | LFVLKDTLKK | MQKFFGLPQT | GDLDQNTIET | 67 |
| MMP-7 | QAQDYLKRF- | YLYDSETK-N | ANSLEAKLKE | MQKFFGLPIT | GMLNSRVIEI | 81 |
| MT-MMP | L-QQYGYLPP | GDLRTHTQRS | PQSLSAAIAA | MQKFYGLQVT | GKADADTMKA | 87 |

Consensus | L-E.Y..L.. | ......E... | ........KL.. | MQKF.GL.VT | GKLD..TL.. | 100

Fig. 2B

| | | | | | |
|---|---|---|---|---|---|
| MMP-11 | LRPPRCGVPD | -PSDGLSARN | RQKRFVLSGG | RWEKTDLTYR | ILRFPWQLVQ | 123 |
| MMP-1 | MKQPRCGVPD | -VAQ-FVL-- | ----TE-GNP | RWEQTHLTYR | IENYTPDLPR | 127 |
| MMP-8 | MKKPRCGVPD | -SGG-FML-- | ----TP-GNP | KWERTNLTYR | IRNYTPQLSE | 126 |
| MMP-10 | MRKPRCGVPD | -VGH-FSS-- | ----FP-GMP | KWRKTHLTYR | IVNYTPDLPR | 126 |
| MMP-3 | MRKPRCGVPD | -VGH-FRT-- | ----FP-GIP | KWRKTHLTYR | IVNYTPDLPK | 127 |
| MMP-9 | MRTPRCGVPD | -LGR-FQT-- | ----FE-GDL | KWHHHNITYW | IQNYSEDLPR | 134 |
| MMP-2 | MRKPRCGNPD | -VAN-YNF-- | ----FP-RKP | KWDKNQITYR | IIGYTPDLDP | 108 |
| MMP-7 | MQKPRCGVPD | -VAE-YSL-- | ----FP-NSP | KWTSKVVTYR | IVSYTRDLPH | 122 |
| MT-MMP | MRRPRCGVPD | KFGAEIKANV | RRKRYAIQGL | KWQHNEITFC | IQNYTPKVGE | 137 |

Consensus  MRKPRCGVPD  -VG.-F.. --  ----FP-G.P  KW..T.LTYR  I.NYTPDLP.  150

| | | | | | |
|---|---|---|---|---|---|
| MMP-11 | EQVRQTMAEA | LKVWSDVTPL | TFTEV----- | ---HEGRADI | MIDFARYWDG | 165 |
| MMP-1 | ADVDHAIEKA | FQLWSNVTPL | TFTKV----- | ---SEGQADI | MISFVRGDHR | 169 |
| MMP-8 | AEVERAIKDA | FELWSVASPL | IFTRI----- | ---SQGEADI | NIAFYQRDHG | 168 |
| MMP-10 | DAVDSAIEKA | LKVWEEVTPL | TFSRL----- | ---YEGEADI | MISFAVKEHG | 168 |
| MMP-3 | DAVDSAVEKA | LKVWEEVTPL | TFSRL----- | ---YEGEADI | MISFAVREHG | 169 |
| MMP-9 | AVIDDAFARA | FALWSAVTPL | TFTRV----- | ---YSRDADI | VIQFGVAEHG | 176 |
| MMP-2 | ETVDDAFARA | FQVWSDVTPL | RFSRI----- | ---HDGEADI | MINFGRWEHG | 150 |
| MMP-7 | ITVDRLVSKA | LNMWGKEIPL | HFRKV----- | ---VWGTADI | MIGFARGAHG | 164 |
| MT-MMP | YATYEAIRKA | FRVWESATPL | RFREVPYAYI | REGHEKQADI | MIFFAEGFHG | 187 |

Consensus  ..VD.A..KA  F.VWS.VTPL  TF.RV-----  ----EG-ADI  MI.FA...HG  200

Fig. 2C

| | | | | | | |
|---|---|---|---|---|---|---|
| MMP-11 | DDLPFDGPGG | ILAHAFFPKT | HREGDVHFDY | DETWTIGDDQ | GTD------- | 208 |
| MMP-1 | DNSPFDGPGG | NLAHAFQPGP | GIGGDAHFDE | DERWTNNFT- | EYN------- | 211 |
| MMP-8 | DNSPFDGPNG | ILAHAFQPGQ | GIGGDAHFDA | EETWTNTSA- | NYN------- | 210 |
| MMP-10 | DFYSFDGPGH | VLAHAYPPGP | GLYGDIHFDD | DEKWTEDAS- | GTN------- | 210 |
| MMP-3 | DFYPFDGPGN | VLAHAYAPGP | GINGDAHFDD | DEQWTKDTT- | GTN------- | 211 |
| MMP-9 | DGYPFDGKDG | LLAHAFPPGP | GIQGDAHFDD | DELWSLGKG- | VVVPTRFGNA | 225 |
| MMP-2 | DGYPFDGKDG | LLAHAFAPGT | GVGGDSHFDD | DELWTLGEG- | QVVRVKYGNA | 199 |
| MMP-7 | DSYPFDGPGN | TLAHAFAPGT | GLGGDAHFDE | DERWTDGSSL | GIN------- | 207 |
| MT-MMP | DSTPFDGEGG | FLAHAYFPGP | NIGGDTHFDS | AEPWTVRNE- | DLN------- | 229 |
| Consensus | D.YPFDGPGG | .LAHAF.PGP | GIGGDAHFD. | DE.WT..... | .N-------- | 250 |
| | | | | | | |
| MMP-11 | ---------- | ---------- | ---------- | ---------- | ---------- | 208 |
| MMP-1 | ---------- | ---------- | ---------- | ---------- | ---------- | 211 |
| MMP-8 | ---------- | ---------- | ---------- | ---------- | ---------- | 210 |
| MMP-10 | ---------- | ---------- | ---------- | ---------- | ---------- | 210 |
| MMP-3 | ---------- | ---------- | ---------- | ---------- | ---------- | 211 |
| MMP-9 | DGAACHFPFI | FEGRSYSACT | TDGRSDGLPW | CSTTANYDTD | DRFGFCPSER | 275 |
| MMP-2 | DGEYCKFPFL | FNGKEYNSCT | DTGRSDGFLW | CSTTYNFEKD | GKYGFCPHEA | 249 |
| MMP-7 | ---------- | ---------- | ---------- | ---------- | ---------- | 207 |
| MT-MMP | ---------- | ---------- | ---------- | ---------- | ---------- | 229 |
| Consensus | ---------- | ---------- | ---------- | ---------- | ---------- | 300 |

Fig. 2D

| | | | | | | |
|---|---|---|---|---|---|---|
| MMP-11 | | | | | | 208 |
| MMP-1 | | | | | | 211 |
| MMP-8 | | | | | | 210 |
| MMP-10 | | | | | | 210 |
| MMP-3 | | | | | | 211 |
| MMP-9 | LYTRDGNADG | KPCQFPFIFQ | GQSYSACTTD | GRSDGYRWCA | TTANYDRDKL | 325 |
| MMP-2 | LFTMGGNAEG | QPCKFPFRFQ | GTSYDSCTTE | GRTDGYRWCG | TTEDYDRDKK | 299 |
| MMP-7 | | | | | | 207 |
| MT-MMP | | | | | | 229 |
| Consensus | | | | | | 350 |

| | | | | | | |
|---|---|---|---|---|---|---|
| MMP-11 | | | | | | 208 |
| MMP-1 | | | | | | 211 |
| MMP-8 | | | | | | 210 |
| MMP-10 | | | | | | 210 |
| MMP-3 | | | | | | 211 |
| MMP-9 | FGFCPTRADS | TVMGGNSAGE | LCVFPFTFLG | KEYSTCTSEG | RGDGRLWCAT | 375 |
| MMP-2 | YGFCPETAMS | TVGG-NSEGA | PCVFPFTFLG | NKYESCTSAG | RSDGKMWCAT | 348 |
| MMP-7 | | | | | | 207 |
| MT-MMP | | | | | | 229 |
| Consensus | | | | | | 400 |

Fig. 2E

| | | | | | |
|---|---|---|---|---|---|
| MMP-11 | -------- | -------L | LQVAA-HEFG | HVLGLQHTTA | AKALMSAFY- | 237 |
| MMP-1 | -------- | -------L | HRVAA-HELG | HSLGLSHSTD | IGALMYPSY- | 240 |
| MMP-8 | -------- | -------L | FLVAA-HEFG | HSLGLAHSSD | PGALMYPNY- | 239 |
| MMP-10 | -------- | -------L | FLVAA-HELG | HSLGLFHSAN | TEALMYPLYN | 240 |
| MMP-3 | -------- | -------L | FLVAA-HEIG | HSLGLFHSAN | TEALMYPLYH | 241 |
| MMP-9 | TSNFDSDKKW | GFCPDQGYSL | FLVAA-HEFG | HALGLDHSSV | PEALMYPMY- | 423 |
| MMP-2 | TANYDDDRKW | GFCPDQGYSL | FLVAA-HEFG | HAMGLEHSQD | PGALMAPIY- | 396 |
| MMP-7 | -------- | -------- | FLYAATHELG | HSLGMGHSSD | PNAVMYPTY- | 236 |
| MT-MMP | -------- | -----GNDI | FLVAV-HELG | HALGLEHSSD | PSAIMAPFY- | 261 |
| Consensus | -------- | -------L | FLVAA-HE.G | HSLGL.HS.D | P.ALMYP.Y- | 450 |
| MMP-11 | TF--RYPLSL | SPDDCRGVQH | LYG------- | ---------- | ---------- | 258 |
| MMP-1 | TF--SGDVQL | AQDDIDGIQA | IYG------- | ---------- | ---------- | 261 |
| MMP-8 | AFRETSNYSL | PQDDIDGIQA | IYG------- | ---------- | ---------- | 262 |
| MMP-10 | SFTELAQFRL | SQDDVNGIQS | LYG------- | ---------- | ---------- | 263 |
| MMP-3 | SLTDLTRFRL | SQDDINGIQS | LYG------- | ---------- | ---------- | 264 |
| MMP-9 | RF--TEGPPL | HKDDVNGIRH | LYGPRPEPEP | RPPTTTTPQP | TAPPTVCPTG | 471 |
| MMP-2 | TY--TKNFRL | SQDDIKGIQE | LYG------- | ---------- | ---------- | 417 |
| MMP-7 | GNGDPQNFKL | SQDDIKGIQK | LYGKRSNSRK | K--------- | ---------- | 267 |
| MT-MMP | QWMDTENFVL | PDDDRRGIQQ | LYGGESGFPT | KMPPQPRTTS | RPSVPDKPKN | 311 |
| Consensus | .F....F.L | SQDDI.GIQ. | LYG------- | ---------- | ---------- | 500 |

Fig. 2F

| | | | | | | |
|---|---|---|---|---|---|---|
| MMP-11 | ------ | ----QPW | PTVTSRTPAL | GPQAGIDTNE | IAPLEPDAPP | 291 |
| MMP-1 | ------ | ------ | RSQNPVQP-I | GPQTP----- | -------KAC | 278 |
| MMP-8 | ------ | ------ | --LSSNP-I | QPTGP---ST | P------KPC | 279 |
| MMP-10 | ------ | -------P | PPASTEEP-L | VPTKS---VP | S-GSEMPAKC | 289 |
| MMP-3 | ------ | -------P | PPDSPETP-L | VPTEP---VP | P-EPGTPANC | 290 |
| MMP-9 | PPTVHPSERP | TAGPTGPPSA | GPTGPPTA-G | PSTAT---TV | PLSPVD-DAC | 516 |
| MMP-2 | ------ | ------ | ---ASPDI-D | LGTGP---TP | TLGPVTPEIC | 440 |
| MMP-7 | ------ | ------ | ------ | ------ | ------ | 267 |
| MT-MMP | PTYGPNICDG | NFDTVAMLRG | EMFVFKKRWF | WRVRNNQVMD | GYPMPIGQFW | 361 |
| Consensus | ------ | ------ | .....P-. | .PT..... | .........C | 550 |

| | | | | | | |
|---|---|---|---|---|---|---|
| MMP-11 | DACEASFDAV | STIR-GELFF | FKAGFVWRLR | GGQL-QPGYP | ALASRHWQGL | 339 |
| MMP-1 | DS-KLTFDAI | TTIR-GEVMF | FKDRFYMR-T | NPFY-PEVEL | NFTSVFWPQL | 324 |
| MMP-8 | DP-SLTFDAI | TTLR-GEILF | FKDRYFWR-R | HPQL-QRVEM | NFISLFWPSL | 325 |
| MMP-10 | DP-ALSFDAI | STLR-GEYLF | FKDRYFWR-R | SHWN-PEPEF | HLISAFWPSL | 335 |
| MMP-3 | DP-ALSFDAV | STLR-GEILI | FKDRHFWR-K | SLRK-LEPEL | HLISSFWPSL | 336 |
| MMP-9 | NV-NI-FDAI | AEIG-NQLYL | FKDGKYWRFS | EGRGSRPQGP | FLIADKWPAL | 563 |
| MMP-2 | KQ-DIVFDGI | AQIR-GEIFF | FKDRFIWRTV | TPRD-KPMGP | LLVATFWPEL | 487 |
| MMP-7 | ------ | ------ | ------ | ------ | ------ | 267 |
| MT-MMP | RGLPASINTA | YERKDGKFVF | FKGDKHWVFD | EASLEPGYPK | HIKELGRG-L | 410 |
| Consensus | D.-...FDAI | .T.R-GE..F | FKDR..WR-. | ......... | .L.S.FWP.L | 600 |

Fig. 2G

| | | | | | | |
|---|---|---|---|---|---|---|
| MMP-11 | P-SPVDAAFE | -DAQGHIWFF | QGAQYWVYDG | EKPVLG---P | APL-TELGLV | 383 |
| MMP-1 | P-NGLEAAYE | FADRDEVRFF | KGNKYWAVQG | QNVLHG--YP | KDIYSSFGFP | 371 |
| MMP-8 | P-TGIQAAYE | DFDRDLIFLF | KGNQYWALSG | YDILQG--YP | KDI-SNYGFP | 371 |
| MMP-10 | P-SYLDAAYE | VNSRDTVFIF | KGNEFWAIRG | NEVQAG--YP | RGI-HTLGFP | 381 |
| MMP-3 | P-SGVDAAYE | VTSKDLVFIF | KGNQFWAIRG | NEVRAG--YP | RGI-HTLGFP | 382 |
| MMP-9 | P-RKLDSVFE | EPLSKKLFFF | SGRQVWVYTG | ASV-LG---P | RRL-DKLGLG | 607 |
| MMP-2 | P-EKIDAVYE | APQEEKAVFF | AGNEYWIYSA | STLERG--YP | KPL-TSLGLP | 533 |
| MMP-7 | -------- | -------- | -------- | -------- | -------- | 267 |
| MT-MMP | PTDKIDAALF | WMPNGKTYFF | RGNKYYRFNE | ELRAVDSEYP | KNIKVWEGIP | 460 |
| Consensus | P-...DAAYE | ........FF | .GN.YW...G | .....G--YP | ..I..LG.P | 650 |

| | | | | | | |
|---|---|---|---|---|---|---|
| MMP-11 | R--FPVHAAL | VWGPEKNKIY | FFRGRDYWRF | HPSTRRVDSP | VPRRATDWRG | 431 |
| MMP-1 | RTVKHIDAAL | S-EENTGKTY | FFVANKYWRY | DEYKRSMDPG | YPKMIAHDFP | 420 |
| MMP-8 | SSVQAIDAAV | F---YRSKTY | FFVNDQFWRY | DNQRQFMEPG | YPKSISGAFP | 418 |
| MMP-10 | PTIRKIDAAV | S-DKEKKKTY | FFAADKYWRF | DENSQSMEQG | FPRLIADDFP | 430 |
| MMP-3 | PTVRKIDAAI | S-DKEKNKTY | FFVEDKYWRF | DEKRNSMEPG | FPKQIAEDFP | 431 |
| MMP-9 | ADVAQVTGAL | R-SGRGKM-L | LFSGRRLWRF | DVKAQMVDPR | SASEVDRMFP | 655 |
| MMP-2 | PDVQRVDAAF | N-WSKNKKTY | IFAGDKFWRY | NEVKKKMDPG | FPKLIADAWN | 582 |
| MMP-7 | -------- | -------- | -------- | -------- | -------- | 267 |
| MT-MMP | ESPRGSFM-G | SDEVFTYFYK | GNKYWKFNNQ | KLKVEPGYPK | SALRDWMGCP | 509 |
| Consensus | ..V...DAA. | .......KTY | FF...K.WR. | D......M.PG | .P..I...FP | 700 |

Fig. 2H

| | | | | | | | |
|---|---|---|---|---|---|---|---|
| MMP-11 | VPSE--IDAA | FQDADGYAYF | LRGRLYWKFD | PVKVKALEGF | PRLV----- | | 473 |
| MMP-1 | GIGH---KVDA | V---FMKDGFF | -----YF-FH | GTRQYKFDPK | TKRILTLQ-- | | 458 |
| MMP-8 | GIES---KVDA | V---FQQEHFF | -----HV-FS | GPRYYAFDLI | AQRVTRVA-- | | 456 |
| MMP-10 | GVEP---KVDA | V---LQAFGFF | -----YF-FS | GSSQFEFDPN | ARMVTHIL-- | | 468 |
| MMP-3 | GIDS---KIDA | V---FEEFGFF | -----YF-FT | GSSQLEFDPN | AKKVTHTL-- | | 469 |
| MMP-9 | GVPL---DTHD | VFQYREKAYF | ---CQDR-FY | WRVSSRSELN | QVDQVGYV-- | | 697 |
| MMP-2 | AIPD---NLDA | VVDLQGGG-- | -----HS-YF | FKGAYYLKLE | N-QSLKSVKF | | 621 |
| MMP-7 | ---------- | ---------- | ---------- | ---------- | ---------- | | 267 |
| MT-MMP | SGGRPDEGTE | EETEVIIIEV | DEEGGAVSA | AAVVLPVLLL | LLVLAVGLAV | | 559 |
| Consensus | G....-..DA | V--........ | ----..-F. | .......... | ---------- | | 750 |

| | | | | | | |
|---|---|---|---|---|---|---|
| MMP-11 | ---GPD-FFG | CAE-----PA | NTFLX----- | ---------- | ---------- | 489 |
| MMP-1 | ---KANSWEN | CR------KN | ---------- | ---------- | ---------- | 469 |
| MMP-8 | ---RGNKWLN | CRY-----GX | ---------- | ---------- | ---------- | 468 |
| MMP-10 | ---KSNSWLH | C-------- | ---------- | ---------- | ---------- | 476 |
| MMP-3 | ---TYD-ILQ | CPE-----DX | ---------- | ---------- | ---------- | 477 |
| MMP-9 | GSIKSD-WLG | C-------- | ---------- | ---------- | ---------- | 708 |
| MMP-2 | ---------- | ---------- | ---------- | ---------- | ---------- | 267 |
| MMP-7 | FFFRRHGTPR | RLLYCQRSLL | DKV------- | ---------- | ---------- | 582 |
| MT-MMP | ---......WL. | C.-------. | ---------- | ---------- | ---------- | 796 |
| Consensus | | | | | | |

METALLOPROTEINASE AND ENCODING DNA THEREFOR

This application is a continuation-in-part of PCT international application No. PCT/JP94/02009 which has an international filing date of Nov. 30, 1994 which designated the United States, the entire contents of which are hereby incorporated by reference.

TECHNICAL FIELD

The present invention relates to a novel metalloproteinase useful in applications such as diagnosis of the presence of tumour cells, diagnosis of the degree of tumour malignancy, or other medical or physiological fields.

More specifically, the present invention relates to one type of metalloproteinase expressed specifically in human tumour cells and a DNA sequence encoding therefor; a plasmid having a nucleotide sequence which contains said DNA sequence; a host cell harbouring said plasmid; a method for manufacturing said protein using said host cell; a probe which hybridizes with the aforesaid DNA sequence; a method for detecting DNA or RNA containing the aforesaid sequence using said probe; and monoclonal antibodies which bind specifically to the aforesaid protein.

BACKGROUND

A group of enzymes with different substrate specificity and referred to in general as matrix metalloproteinases (hereinafter referred to as "MMPs") contributes to degradation of the extracellular matrix comprising such complex components as collagen, proteoglycan, elastin, fibronectin, and laminin.

Previously reported MMPs include interstitial collagenase (MMP-1), 72 kDa gelatinase (also known as type IV collagenase or gelatinase A; MMP-2), 92 kDa gelatinase (also known as type IV collagenase or gelatinase B; MMP-9), stromelysin-1 (MMP-3), matrilysin (MMP-7), neutrophil collagenase (MMP-8), stromelysin-2 (MMP10) and stromelysin-3 (MMP-11).

These MMPs are a family of enzymes whose primary structure has been reported previously. With the exception of MMP-7, the primary structure among the family of reported MMPs comprises essentially an N-terminal propeptide domain, a $Zn^+$ binding catalytic domain and a C-terminal hemopexin-like domain. In MMP-7 there is no hemopexin-like domain. MMP-2 and MMP-9 contain an additional gelatin-binding domain. In addition, a proline-rich domain highly homologous to a type V collagen α2 chain is inserted in MMP9 between the $Zn^+$ binding catalytic domain and the C-terminal hemopexin-like domain.

In highly metastatic tumour cells, there are reports of conspicuous expression of type IV collagenase (MMP-2, MMP-9) which mainly degrade type IV collagen (Cancer Res., 46:1–7, 1986; Biochem. Biophys. Res. Commun., 154:832–838, 1988; Cancer, 71:1368–1383, 1993). Likewise, it has been reported MMP-3 act as an activator of proMMP-9 (J. Biol. Chem., 267:3581–3584, 1992).

The degree of matrix metalloproteinase expression serves as an index to diagnosing the degree of cancer malignancy.

DISCLOSURE OF THE INVENTION

The present inventors discovered a novel matrix metalloproteinase (hereinafter referred to as "MT-MMP") and performed a structural analysis thereof.

As described hereafter, the present invention offers a novel metalloproteinase protein, DNA having a nucleotide sequence which encodes said protein, a plasmid having said DNA nucleotide sequence, a host cell harbouring said plasmid and monoclonal antibodies which specifically recognize the aforesaid metalloproteinase protein.

1. A native membrane-type matrix-metalloproteinase characterized by a continuous sequence of hydrophobic amino acids peculiar to membrane-binding proteins from amino acid number 533 to 562 in the C terminus domain shown in SEQ ID NO:1.

2. A native membrane-type matrix-metalloproteinase according to claim 1, characterized by the amino acid sequence from amino acid number 160 to 173, 320 to 333 and from 498 to 512 shown in SEQ ID NO:1.

3. A native membrane-type matrix-metalloproteinase according to claim 1, characterized by the amino acid sequence from amino acid number 1 to 173, 320 to 333, 498 to 512 and 563 to 582 shown in SEQ ID NO:1.

4. A DNA having the nucleotide sequence shown in SEQ ID NO:2 which corresponds to the amino acid sequence of a membrane-type matrix-metalloproteinase according to claim 1, 2 or 3.

5. A plasmid containing a DNA having the nucleotide sequence according to claim 4 and expressing a membrane-type matrix-metalloproteinase according to claim 1, 2 or 3.

6. A host cell harbouring a plasmid containing a DNA having the nucleotide sequence according to claim 4, and expressing a membrane-type matrix-metalloproteinase according to claim 1, 2 or 3.

7. Monoclonal antibodies which peculiarly recognize a membrane-type matrix-metalloproteinase according to claim 1, 2 or 3.

8. A protein having the amino acid sequence shown in SEQ ID NO:1.

9. A DNA having the nucleotide sequence shown in SEQ ID NO:2 which encodes a protein having the amino acid sequence shown in SEQ ID NO:1.

10. A plasmid containing a DNA having the nucleotide sequence shown in SEQ ID NO:2, and expressing the protein shown in SEQ ID NO:1.

11. A host cell harbouring a plasmid containing a DNA having the nucleotide sequence shown in SEQ ID NO:2, and expressing the protein shown in SEQ ID NO:1.

12. Monoclonal antibodies which peculiarly recognize a protein having the amino acid sequence shown in SEQ ID NO: 1.

The present invention is described in detail hereafter.

Using highly conserved sequences (SEQ ID NOS:3 and 4) selected from amino acid sequences of the known matrix metalloproteinase (MMP) family, the present inventors designed and synthesized an oligonucleotide primer having the sequences denoted by SEQ ID NOS:5 and 6. A PCR was carried out using said oligonucleotide primer and a human placental cDNA library, the PCR products obtained were sequenced, and a 390 bp DNA fragment having a sequence non-homologous to known MMP was obtained. Using this 390 bp DNA fragment as a probe, the human placenta cDNA library was screened, and a cDNA in the positive phage clone obtained was sequenced. The nucleotide sequence is that denoted by SEQ ID NO:2. A sequence identical to the nucleotide sequence in SEQ ID NO:2 did not exist in the Genbank/EMBL DNA database, and DNA having this nucleotide sequence was ascertained to be completely novel.

The nucleotide sequence of the aforesaid cloned cDNA in SEQ ID NO:2 had a 3' non-coding sequence and open reading frame that potentially encode 582 amino acid. An initiation codon was located at nucleotide number 112, and a stop codon was present at nucleotide number 1858. It was determined that this open reading frame encoded the 582 amino acid sequence in SEQ ID NO:1, that a deduced signal sequence continued after the initiation codon, and that a hydrophobic domain (SEQ ID NO:7) specific to a membrane-binding protein of 20 or more linked hydrophobic amino acids was present from C-terminal amino acid number 533 to 562.

When homology between the amino acid sequence of MT-MMP and that of the known MMP family was analyzed, MT-MMP had high homology to the known MMP family, as shown in FIG. 2. The sequences best conserved in MT-MMP were active site sequences, as well as sequences proximal to processing site between precursor and mature substance conserved in the MMP family. The fact that MT-MMP has the structural characteristics of a membrane-binding protein, and the presence in MT-MMP of a sequence of linked hydrophobic amino acids (shown in Sequence Sheet sequence number 7) not found in the rest of the MMP family, strongly suggested that MT-MMP, unlike other MMP family, is a membrane-binding MMP.

When MT-MMP expression in various human tissues was studied by Northern Blot analysis with various tissue-derived Poly(A)RNA, high expression was seen in the placenta, lung and kidney (see FIG. 3). Likewise, results from Northern Blot analysis performed with RNA extracted from normal and tumour areas of human lung squamous cell carcinoma showed that MT-MMP is expressed peculiarly at tumour sites (see FIG. 4).

Finally, immunoprecipitation and immunostain experiments using anti-MT-MMP monoclonal antibodies showed that the MT-MMP pertaining to the present invention is expressed on a cell membrane without secretion of a gene product, and MMP-2 activation induced by the expression of MT-MMP was observed in the cells transfected with MT-MMP gene (Nature, 370:61–65, 1994).

Due to the achievements of the above-discussed research by the present inventors, the present invention offers a novel matrix metalloproteinase protein having the amino acid sequence in SEQ ID NO:1.

In addition, the present invention offers DNA having the nucleotide sequence in SEQ ID NO:2, which encodes a protein having the amino acid sequence in SEQ ID NO:1; a plasmid containing and capable of expressing said DNA; and a host cell harbouring said plasmid. All host cells used in general recombinant DNA technology can be used as the aforementioned host cell, including prokaryotes such as *E. coli* and *Bacilus subtilus;* eukaryotes such as yeast, COS cells, CHO cells and 3T3 cells; and insect cells such as Sf21. Expression vectors corresponding to used host cells can be used as the aforementioned plasmid.

Furthermore, the present invention offers mRNA transcribed from DNA having the nucleotide sequence in SEQ ID NO:2.

The present invention also offers a probe which hybridizes with the aforementioned DNA or RNA and specifically detects said DNA or RNA, and said probe may be one having any part of the nucleotide sequence in SEQ ID NO:2, provided said probe is labeled by a generally used radioactive isotope or enzyme or the like, hybridizes specifically with said DNA or RNA in general blotting analysis and in situ hybridization, and accomplishes detection.

Furthermore, the present invention offers monoclonal antibodies which bind peculiarly with the MT-MMP pertaining to the present invention.

The monoclonal antibodies pertaining to the present invention can be prepared by a well-known method such as the method of Milstein et al. (Nature, 256:495–497, 1975) using human MT-MMP as an antigen. In this method, the antigen may be native human MT-MMP, recombinant human MT-MMP, or a synthetic peptide having a partial amino acid sequence of either.

By means of the present invention, DNA having a nucleotide sequence which encodes a protein with the amino acid sequence of the novel MT-MMP pertaining to the present invention can be cloned, and such DNA and a protein encoded by such DNA can be prepared by a genetic engineering technique. Through the use of a cDNA clone of such a novel MT-MMP, techniques generally used in genetic engineering can be used to clone the aforementioned nucleotide sequence into another vector or host. Based on the aforementioned cDNA nucleotide sequence, DNA appropriately suited to a probe may be designed and prepared. In addition, based on the nucleotide sequence of the MT-MMP pertaining to the present invention, techniques generally used in genetic engineering can be used to prepare a corresponding protein wherein appropriate mutation have been introduced into the MT-MMP amino acid sequence by substitution, deletion, insertion, displacement or addition of one or more amino acids. All such aforementioned derivatives may also be included in the present invention, provided that common metalloproteinase characteristics are conserved; namely, sequences proximal to processing site between precursor and mature substance, active site sequences and domain structure, and provided that the MT-MMP characteristic of a hydrophobic domain of linked hydrophobic amino acids present near the C terminus is conserved.

Use of the above-discussed various implementations of the present invention offers various technical means applicable to applications pertaining to diagnostic agents or diagnostic methods used for diagnosis of the presence of tumour cells or for diagnosis of the degree of tumour malignancy, as well as applications in other medical or physiological fields.

The present invention is described in detail hereafter by means of Working Examples, but the present invention is not limited by these Working Examples.

WORKING EXAMPLES

Working Example 1

Isolation of Novel Metalloproteinase (MT-MMP) cDNA (a) Construction of cDNA Library Total RNA was extracted from human placenta tissue by a guanidine-cesium chloride method (Biochemistry, 18:5294–5299, 1979) and poly(A)$^+$RNA was purified using an oligo(dT)cellulose column. Using a purified poly(A)$^+$ RNA as a template and an oligo(dT) primer, cDNA was synthesized according to the Gubler-Hoffman method (Gene, 25:263–269, 1983). The ends of the cDNA were converted to blunt end with T$_4$ DNA polymerase, and EcoR I sites present in the cDNA were methylated by EcoR I methylase. Using T$_4$ DNA ligase, an EcoR I linker [d(pG-G-A-A-T-T-C-C)] and the cDNA were ligated, and cDNA possessing EcoR I sites at both ends was generated by EcoR I digestion. Using T$_4$ DNA ligase, this cDNA was cloned into EcoR I site of λgt11. In vitro packaging of this cDNA was carried out, for example, using an in vitro packaging kit (Amersham), and a cDNA library was thus constructed. A commercial cDNA library such as a human placenta cDNA library (Clontech) can be used as a cDNA library.

(b) Preparation of synthetic oligonucleotide primer

The sequences denoted by Sequence SEQ ID NOS:3 (P-1) and 4 (P-2) were selected from among amino acid sequences of the known MMP family as highly conserved amino acid sequences in the MMP family, and oligodeoxynucleotide primers corresponding respectively to oligopeptide P-1 and oligopeptide P-2 were designed. Specifically, when amino acids coded by two or more codons were present in an oligopeptide, the sequences were designed as a mixture as shown in SEQ ID NOS:5 (primer 1) and 6 (primer 2). Primer 1 and primer 2 were synthesized by a β-cyanoethyl phosphoamidite method using a DNA synthesizer (Applied Biosystems Model 392). Using a NICK column (Pharmacia) equilibrated with 10 mM sodium phosphate buffer, pH 6.8 the obtained primer 1 and primer 2 were purified.

(c) Gene amplification by PCR

Using a human placenta-derived cDNA as a template and primers 1 and 2 noted in the above section (b), a PCR (PCR Technology, Stockton Press, pp. 63–67, 1989) was run.

As a result, a 390 bp PCR product was yielded. The obtained PCR product was cloned in an appropriate plasmid, e.g., pUC 119 or pBluescript, and the nucleotide sequence of the PCR product was determined using a fluorescence DNA sequencer (Applied Biosystems, Model 373A) and a Taq dye-primer cycle sequencing kit (Applied Biosystems). Among various PCR products whose nucleotide sequences were determined, PCR product A having no homology to nucleotide sequences of previously reported MMPs was obtained. PCR product A was used as a probe for screening the human placenta cDNA library noted in the foregoing section (a). $^{32}$P labeling of the probe was generated using a random primed DNA labeling kit (Boehringer Mannhaim).

(d) Screening of novel MMP gene from cDNA library and DNA sequencing.

Host *E. coli* Y1090 was transfected with the human placenta cDNA library constructed in the λgtll cited in the foregoing section (a) and plaques were formed. Specifically, Y1090 was cultured overnight in an L broth containing 0.02% maltose, and bacteria were harvested and suspended in 10 mM MgSO$_4$. This cell suspension and a phage solution were mixed, incubated at 37° C. for 15 minutes, and then the phages were adsorbed onto the host bacteria. Soft agar was added thereto, and the material was spread on an L plate (the above-noted operation is hereinafter termed "plating"). The plate was incubated overnight at 42° C. and a plaque was formed, after which a nylon filter (e.g., Hibond-N, Amersham) or a nitrocellulose filter (e.g., HATF, Millipore) was placed onto the plate and left in place for approximately 30 seconds. The filter was gently peeled and immersed in an alkaline denaturant (0.1 M NaOH, 1.5 M NaCl) for 30 seconds, then immersed in a neutralizing solution (0.5 M Tris-HCl buffer, pH 8 containing 1.5 M NaCl) for 5 minutes. The filter was then washed with 2× SSPE (0.36 M NaCl, 20 mM NaH$_2$PO$_4$, 2 mM EDTA) and dried. The foregoing plaque-to-filter transfer was repeated, and at least two filters were prepared. However, plate contact time for the second and subsequent filters was extended to approximately 2 minutes. Filters were baked 2 hours at 80° C. and DNA was thus fixed. The two filters, at a minimum, prepared from one plate were respectively washed 1 hour at 42° C. in a wash solution (50 mM Tris-HCl buffer, pH 8.0 containing 1 M NaCl, 1 mM EDTA and 0.1% SDS), placed in a hybridization bag, and prehybridization was carried out by 6 to 8 hours immersion at 42° C. in a prehybridization solution [50% formamide, 5×Denhardt's solution (0.2% bovine serum albumin, 0.2% polyvinylpyrolidone), 5× SSPE, 0.1% SDS, 100 μg/ml heat-denatured salmon sperm DNA]. Next, the $^{32}$P-labeled probe noted in section (c), heat-denatured for 5 minutes at 100° C., was added to the prehybridization solution, and hybridization was carried out overnight at 42° C. After hybridization was complete, the filters were washed at room temperature with an excess of 2× SSC solution containing 0.1% SDS. Next, the filters were placed for 15 minutes at 68° C. in 1× SSC solution containing 0.1% SDS. The filters were then dried, layered with X-ray film (Kodak XR), and 1 week autoradiography was then carried out at −70° C. The X-ray films were developed, replica filters in duplicate produced from one plate were piled up each other, and signals that appeared precisely same place on duplicate filters were marked. Plaques corresponding to marked signals were suspended in SM solution (50 mM Tris-HCl buffer, pH 7.5 containing 0.1 M NaCl and 10 mM MgSO$_4$). These phage suspensions were appropriately diluted and plating was performed, screening similar to that noted above was carried out, and recombinant phages were obtained.

(e) Preparation of recombinant λgtll DNA

Each cloned phages was plated, incubated for 3 hours at 42° C., and incubated overnight at 37° C. Several drops of chloroform was then added to the SM solution and the material was left at room temperature for 30 minutes. The SM solution together with the upper layer of soft agar was then scraped off, and centrifuged. Polyethylene glycol was added to a 10% final concentration in the supernatant, and the material was mixed and left at 4° C. for 1 hour. The material was then centrifuged, the supernatant was discarded, and phage particles were collected. The phage particles were suspended in SM solution and purified by a glycerol gradient ultracentrifugation method (see "Molecular Cloning, a Laboratory Manual", T. Maniastis et al., Cold Spring Harbor: Laboratory Press pp. 2.78, 1989). The phages obtained were suspended in SM solution and treated with DNase I and RNase A. A mixture of 20 mM EDTA, 50 μg/ml proteinase K, and 0.5% SDS was then added, and the material was incubated at 65° C. for 1 hour. The material was then subjected to phenol extraction and diethylether extraction, and DNA was precipitated by ethanol precipitation. The DNA obtained was washed with 70% ethanol, dried, and dissolved in TE solution (10 mM Tris-HCl buffer, pH 8 containing l0mM EDTA).

(f) Sequencing of the insertion fragment

The μgtll DNA prepared in the above section (e) was digested with EcoR I, an insertion fragment was excised and purified, and cloned into the EcoR I site of a pBluescript (Stratagene) vector. *E. coli* NM522 XLI-Blue (Deposited in the National Institute of Bioscience and Human-Technology as Deposit No. P-15032). was transformed with this recombinant pBluescript. The F' transformed cells were selected, infected with helper phage VCSM13 (Stratagene), and cultured overnight. The culture was centrifuged and the bacteria were removed, and PEG/NaCl was added to precipitate the phages. The precipitate was suspended in TE solution, and single-stranded DNA was extracted with phenol and recovered by ethanol precipitation. The single-stranded DNA was sequenced using a fluorescence DNA sequencer (Applied Biosystems, Model 373A) and a Taq dye-primer cycle sequencing kit (Applied Biosystems). The total length of the sequence determined was 3403 base pairs, and the sequence thereof is denoted by SEQ ID NO:2. The nucleotide sequence in SEQ ID NO:2 was searched using the Genbank/EMBL DNA database, but an identical sequence did not exist.

(g) Analysis of Gene Product

Hydrophilic and hydrophobic values of the amino acid sequence denoted by SEQ ID NO:1, as predicted from the nucleotide sequence denoted by SEQ ID NO:2, were calculated by the KyteDoolittle method (J. Mol. Biol., 157:105–132, 1982), and the hydrophilic and hydrophobic distribution plot shown in FIG. 1 was determined. A hydrophobic domain comprising a sequence of 20 or more linked hydrophobic amino acids peculiar to a membrane binding protein was present from position 533 to position 562 of the C-terminal region of SEQ ID NO:1, and the sequence thereof is shown in SEQ ID NO:7. Such a sequence of linked hydrophobic amino acids does not exist in previously known MMPs.

When the homology of the amino acid sequence in SEQ ID NO:1 was compared to reported MMPs amino acid sequences, the amino acid sequence in SEQ ID NO:1 showed homology with the MMP family. Specifically, processing site between precursor and active enzyme and active site conserved to an extremely high degree among MMP family were each highly conserved in MT-MMP as well (SEQ ID NO:1, amino acids numbers 88–97 and 112–222).

Working Example 2

Gene Expression (a) Expression in Tissues

Using $^{32}$P-labeled PCR product A noted in Working Example 1, section (c) as a probe, hybridization was performed with poly(A)$^+$ RNA blotted membrane, human multiple tissue Northern Blots (Clontech), which contains poly (A)$^+$ RNA from human heart, brain, placenta, lung, liver, skeletal muscle, kidney and pancreas. Human multiple tissue Northern Blot filters wetted with 3× SSC (0.45 M NaCl, 0.045 M trisodium citrate·2H$_2$O, pH 7.0) were prehybridized for 2 to 3 hours in a prehybridization solution (0.75 M NaCl, 2.5 mM EDTA, 0.5× Denhardt's solution, 50% formamide and 20 mM Tris-HCl buffer, pH 7.5 containing 1% SDS) with gentle agitation. Next, a heat-denatured probe was added to the hybridization solution (10% sodium dextran and 50 µg/ml denatured salmon sperm DNA-containing prehybridization solution), the prehybridization solution was replaced, and hybridization was performed overnight at 43° C. After hybridization was complete, the filters were washed with 2× SSC containing 0.1% SDS. Next, the filters were placed for 15 minutes at 68° C. in 1× SSC containing 0.1% SDS. The filters were then dried, layered with X-ray film (Kodak XR), and 1 week autoradiography was then carried out at −70° C. The size of the MT-MMP gene transcripts was 4.8 kb in each tissue. When the developed X-ray films were traced by a densitometer and signal intensity was measured, among the investigated tissues, MT-MMP genes were found to be highly expressed in the lung, placenta and kidney.

(b) Expression in Tumour Tissues

Normal and tumour tissues were taken from samples of two squamous cell carcinomas human lung, respectively, and total RNA was extracted by a guanidine-cesium chloride method. 10 µg of each said RNA was applied to 1% agarose electrophoresis and then transferred onto a nylon membrane. Hybridization was then carried out with the $^{32}$P-labeled probe noted in Working Example 1, section (c). Hybridization and autoradiography tracing were performed as described in the foregoing section (a). In each human lung squamous cell carcinoma, significantly higher expression were seen in tumour tissue (see FIG. 4 T) than in normal tissue (see FIG. 4 N).

Working Example 3

Preparation of Monoclonal Antibodies (a) Preparation of Polypeptides as Antigen

From the MT-MMP amino acid sequence denoted by SEQ ID NO:1, sequences denoted by SEQ ID NOS:8, 9 and 10 (sequence of SEQ ID NO:1 amino acid numbers 160–173, 320–333, and 498–512, respectively; hereinafter termed polypeptide A, polypeptide B and polypeptide C, respectively) were selected as specific sequences having low homology to other members of MMP family. These polypeptides were synthesized by Fmoc-BOP method using a peptide synthesizer (MilliGen/Biosearch, Peptide Synthesizer 9600), and cysteine was introduced at the N-terminus. Each synthesized peptide was purified by high speed liquid chromatography.

(b) Preparation of Each Polypeptides and Keyhole Limpet Hemocyanin Complexes 2 mg of keyhole limpet hemocyanin (KLH) dissolved in 1 ml of 0.1 M phosphate buffer, pH 7.5 and 1.85 mg N-(ε-maleimidocaproyloxy)succinimide dissolved in 200 µl dimethylformamide were mixed and incubated at 30° C. for 30 minutes. Next, the above-noted mixture was applied to gel filtration by PD-10 (Pharmacia) equilibrated with 0.1 M phosphate buffer, pH 7.0. KLH-bound maleimide was collected and concentrated to less than 1.5 ml. Each polypeptide synthesized in the foregoing section (a) was respectively dissolved in 1 ml of 0.1 M phosphate buffer, pH 7.0 and mixed with KLH-bound maleimide at a molar ratio representing a factor of 50. This material was then incubated 20 hours at 4° C., and KLH-polypeptide complexes were thus prepared.

(c) Preparation of Antibody-producing Cells

As an initial immunization, eight-week-old Balb/c female mice were given an intraperitoneal administration of 250 µg of a complex of KLH and, respectively, polypeptide A, polypeptide B or polypeptide C prepared in the above section (b), in Freund's complete adjuvant. After 18 days, the respectively immunized mice were boosted intraperitoneally with 200 µg of the respective complexes dissolved in 0.1 M phosphate buffer, pH 7.5. After 32 days, a final immunization of 100 µg of each complex was administered intravenously as the booster immunization. Three days thereafter, splencytes were extirpated and splencyte suspensions were prepared.

(d) Cell Fusion

Fusion with 8-azaguanine-resistant myeloma cell SP2 (SP2/O-Ag14) was performed according to a modifying method of Oi et al (see Selected Methods in Cellular Immunology, Mishell, B. B. and Shiigi, S. M., ed., W. H. Freeman and Company pp. 351–372, 1980). Fusion of myeloma cell SP2 with karyo-splencytes from mice immunized with the polypeptide AKLH complex is discussed in details, hereafter.

Through the following procedures, karyo-splencytes prepared in the foregoing section (c) (cell viability 100%) were fused in a 5:1 ratio with myeloma cells (cell viability 100%). A polypeptide A-immunized splencyte suspension and myeloma cells were separately washed in RPMI 1640 medium. The material was then suspended in the same medium, and 3×10$^8$ cells of karyo-splencytes and 6×10$^7$ cells of myeloma cells were mixed for fusion. The cells were then precipitated by centrifugation, and all the supernatant was completely discarded by suction. 2.0 ml of PEG 4000 solution (RPMI 1640 medium containing 50% [w/v] polyethylene glycol 4000) prewarmed at 37° C. was added dropwise to the precipitated cells over 1 minute, 1 minute stirring was performed, and the cells were resuspended and dispersed. Next, 2.0 ml of RPMI 1640 medium prewarmed at 37° C. was added in a dropwise fashion over 1 minute. After repeating the same operation once more, 14 ml of RPMI 1640 medium was added dropwise over 2 to 3 minutes under constant stirring, and the cells were dispersed. The dispersion was centrifuged and the supernatant was completely discarded by suction. Next, 30 ml of NS-1 medium (RPMI 1640 medium containing filter-sterilized 15% [w/v] fetal calf serum [JRH Biosciences]) prewarmed at 37° C. was rapidly added to the precipitated cells, and the large cell clumps were carefully dispersed by pipetting. The dispersion was then diluted by adding 30 ml of NS-1 medium, and $6.0\times10^5$ cells/0.1 ml/well was added to a polystyrene 96-microwell plate. The above-noted cell-filled microwells were cultured in 7% carbonic acid gas/93% atmospheric air at 37° C. and 100% humidity.

In the case of splencytes derived from mice immunized with the polypeptide B-KLH complex, $6.4\times10^8$ cells of splencytes and $1.28\times10^8$ cells of myeloma cells were mixed, and respectively, 4.3 ml, 38.7 ml and 129 ml of the above-used PEG 4000 solution, RPMI 1640 medium and NS-1 medium were used. In the case of splencytes derived from mice immunized with the polypeptide C-KLH complex, $6.8\times10^8$ cells of splencytes and $1.36\times10^8$ cells of myeloma cells were mixed, and 4.5 ml, 40.5 ml and 135 ml of respectively PEG 4000 solution, RPMI 1640 medium and NS-1 medium were used.

(e) Selective Amplification of Hybridomas by Selective Culture Medium

On the day following the start of culturing mentioned in the above section (d) (Day 1), 2 drops (approx. 0.1 ml) HAT culture medium (100 $\mu$M hypoxanthine, 0.4 $\mu$M aminopterin and 16 $\mu$M thymidine added to NS-1 culture medium) were added to the cells with a Pasteur pipette. On Days 2, 3, 5 and 8, half of each culture medium (approx. 0.1 ml) was replaced with fresh HAT medium, and on Day 11, half of each culture medium was replaced with fresh HT culture medium (HAT culture medium not containing aminopterin). On Day 14, for all the wells in which hybridoma growth was observed to the naked eye, positive wells were investigated by enzyme-linked immunoadsorbent assay (ELISA). Specifically, the polystyrene 96-well plate was respectively coated with polypeptides A, B and C serving as antigens, washed using PBS for washing (containing 0.05% Tween 20), and unadsorbed peptides were thus removed. In addition, the uncoated portion of each well was blocked with 1% BSA. 0.1 ml of supernatant from wells in which hybridoma growth was confirmed was added to each polypeptide-coated well, and the plate was stood at room temperature for approximately 1 hour.

Horseradish peroxidase-labeled goat anti-mouse immunoglobulin was added as a secondary antibody, and the plate was again stood at room temperature for approximately another 1 hour. A substrate of hydrogen peroxide and o-phenylenediamine was added, and the degree of color development was measured as absorbance at 492 nm using a microplate light absorbency measuring device (MRP-A4, Tosoh).

(f) Hybridoma Cloning

Hybridomas in wells positive with respect to individual antigen peptides, as obtained in the foregoing section (e), were monocloned according to the limiting dilution method. Specifically, hybridomas were diluted to 5, 1 and 0.5 per well and were respectively added to 36, 36 and 24 wells of a 96 microwells. On Day 5 and Day 12, approximately 0.1 ml NS-1 medium was added to each well. Approximately 2 weeks after cloning began, the ELISA noted in section (e) was performed for groups in which sufficient hybridoma growth was visually confirmed and 50% or more wells were negative for colony formation. If all tested wells were not positive, 4 to 6 antibody-positive wells in which the number of colonies was 1 were selected, and recloning was performed. Finally, as shown in Table 1 and Table 2, 12, 20 and 9 hybridomas were obtained which produced monoclonal antibodies against polypeptide A, polypeptide B or polypeptide C, respectively.

(g) Hybridoma Culturing and Monoclonal Antibody Purification

Each obtained hybridoma was cultured in NS-1 medium and a 10 to 100 $\mu$g/ml concentration of monoclonal antibody was successfully obtained from the supernatant thereof. In addition, BALB/c mice given an one week prior intraperitoneal administration of pristane were given a similar intraperitoneal administration of $1\times10^7$ cells of obtained hybridomas, and after 1 to 2 weeks, abdominal fluid containing 4 to 7 mg/ml of monoclonal antibody was successfully obtained. The abdominal fluid obtained was salted out by 40% saturated ammonium sulfate, and IgG class antibodies were adsorbed to Protein A Affigel (Bio-Rad) and purified by elution with a 0.1M citric acid buffer, pH 5.

(h) Determination of Monoclonal Antibody Class and Subclass

In accordance with the above-discussed ELISA, the supernatant of monoclones obtained in section (f) were added to microtitration plates respectively coated with polypeptide A, polypeptide B or polypeptide C. After washing with PBS, isotype-specific rabbit anti-mouse IgG antibodies (Zymed Lab.) were added. After washing with PBS, horseradish peroxidase-labeled goat anti-rabbit IgG (H+L) was added, and class and subclass were determined using hydrogen peroxide and 2.2'-azino-di(3-ethylbenzthiazolinic acid) as a substrate.

(i) Specificity of Anti-MT-MMP Monoclonal Antibodies

The cross-reactivity of five varieties of anti-MT-MMP monoclonal antibodies (monoclone numbers 113-5B7, 113-15E7, 114-1F1, 114-2F2 and 118-3B1) exhibiting a positive reaction against a human MT-MMP peptide was determined by the ELISA noted in the foregoing section (e), using as respective antigens: proMMP-1 (Clin. Chim. Acta, 219:1–14, 1993), proMMP-2 (Clin. Chim. Acta, 221:91–103, 1993) and proMMP-3 (Clin. Chim. Acta, 211:59–72, 1992) respectively purified from the supernatant of nomal human skin fibroblast (NB1RGB) culture; proMMP-7 purified from the supernatant of human rectal carcinoma cell (CaR-1) culture (Cancer Res., 50:7758–7764, 1990), proMMP-8 purified from human neutrophils (Biol. Chem. Hoppe-Seyler, 371 supp:295–304, 1990) and proMMP-9 purified from the supernatant of human fibrosarcoma cells (HT1080) culture (J. Biol. Chem., 267: 21712–21719, 1992).

Specifically, using a polystyrene 96-well plate, each well was coated by adding 50 ng/well of purified MMP-1, MMP2, MMP-3, MMP-7, MMP-8 and MMP-9, respectively. Washing was performed with PBS for washing and non-adsorbed antigen was removed, and the uncoated portion of each well was blocked with PBS containing 3% skim milk. 1 $\mu$g/well of each MT-MMP monoclonal antibody was respectively added to each well and stood at room temperature for approximately 1 hour. After washing plate, peroxidase-labeled goat anti-mouse immunoglobulin was added as a secondary antibody, and the plate was again stood at room temperature for approximately 1 hour. A substrate of hydrogen peroxide and o-phenylene diamine was added, and the degree of color development was measured absorbance at 492 nm using a microplate light absorbency measuring device (MRP-A4, Tosoh).

In results, as shown in Table 3, each anti-MT-MMP monoclonal antibody showed no reactivity against purified MMPs other than the MT-MMP supplied for testing.

TABLE 1

| Polypeptide | Monoclone No. | Subclass/Chain |
|---|---|---|
| A | 114-1F2 | γ1/κ |
|   | 114-2F2 | γ1/κ |
|   | 114-3H7 | γ1/κ |
|   | 114-5E4 | γ1/κ |
|   | 114-6G6 | γ1/κ |
|   | 114-8D10 | γ1/κ |
|   | 114-9H3 | μ/κ |
|   | 114-15E8 | γ1/κ |
|   | 114-16C11 | γ1/κ |
|   | 114-18E4 | γ1/κ |
|   | 114-19F11 | γ1/κ |
|   | 114-20H5 | μ/κ |
| B | 113-1E3 | γ3/κ |
|   | 113-2E9 | γ3/κ |
|   | 113-3F6 | γ2b/κ |
|   | 113-4H7 | γ3/κ |
|   | 113-5B7 | γ3/κ |
|   | 113-7C6 | γ2b/κ |
|   | 113-9G9 | γ3/κ |
|   | 113-10F2 | γ3/κ |
|   | 113-13G11 | γ3/κ |
|   | 113-15E7 | γ3/κ |
|   | 113-16H8 | γ3/κ |
|   | 113-17G12 | μ/κ |
|   | 113-19A10 | μ/κ |
|   | 113-20G11 | γ3/κ |
|   | 113-21H3 | γ1/κ |
|   | 113-26D3 | μ/κ |
|   | 113-44C1 | γ1/κ |
|   | 113-46B7 | γ1/κ |
|   | 113-53G5 | μ/κ |
|   | 113-63E8 | γ1/κ |

TABLE 2

| Polypeptide | Monoclone No. | Subclass/Chain |
|---|---|---|
| C | 118-3B1 | γ2b/κ |
|   | 118-6F3 | γ2b/κ |
|   | 118-8D11 | γ1/κ |
|   | 118-9B11 | γ1/κ |
|   | 118-13D11 | α/κ |
|   | 118-18C12 | γ1/κ |
|   | 118-20A3 | γ2b/κ |
|   | 118-25C3 | γ1/κ |
|   | 118-26F5 | γ3/κ |

TABLE 3

| Monoclone No. | Cross reactivity | | | | | |
|---|---|---|---|---|---|---|
|   | MMP-1 | MMP-2 | MMP-3 | MMP-7 | MMP-8 | MMP-9 |
| 113-5B7 | — | — | — | — | — | — |
| 113-15E7 | — | — | — | — | — | — |
| 114-1F2 | — | — | — | — | — | — |
| 114-2F2 | — | — | — | — | — | — |
| 118-3B1 | — | — | — | — | — | — |

—: No reaction

Working Example 4

Expression and Identification of Gene Product

By means of EcoR I cleavage, an insertion fragment was excised from the recombinant pBluescript containing a cloned MT-MMP gene, constructed in section (f) of Working Example 1. Cloning was then carried out at an EcoR I site of the eukaryotic expression vector pSG5 (Stratagene) Then, human fibrosarcoma cells (HT1080) were transfected with said recombinant pSG5 by a calcium phosphate method. Specifically, 20 μg of recombinant pSG5 and 62 μl of 2M $CaCl_2$ was added to distilled water, and 2× HBSP solution (50 mM HEPES buffer, pH 7.1 containing 1.5 mM $Na_2HPO_4$, 10 mM KCl, 280 mM NaCl and 12 mM glucose) was added to the bottom of the tube to form a total volume of 1 ml. This material was mixed, stood at room temperature for approximately 30 minutes, and thorough precipitate formation was carried out. The precipitate was dispersed by pipetting, added dropwise to HT1080 cells and incubated for approximately 4 hours in a $CO_2$ incubator. Next, the culture medium was removed, a 15% glycerol solution was added and treated for 1 to 3 hours, the glycerol was discarded by suction, washed with PBS and fresh culture medium containing $^{35}$S-methionine was added. Culturing was continued, and cellular proteins were labeled by $^{35}$S. Incidentally, expression of MT-MMP genes in HT1080 cells cannot be detected by Northern Blot analysis.

The cells were incubated for 1 hour at 4° C. in a lysing buffer solution (0.01 M Tris-HCl buffer, pH 8 containing 1% Triton X-100, 1% bovine hemoglobin, 1 mM iodoacetamide, 0.2U trypsin inhibitor, 1 mM PMSF and 0.14 M NaCl). The cell lysate was centrifuged and the supernatant was recovered. Sepharose-4B (Pharmacia) coupled with a monoclonal antibody obtained in Working Example 3 was added to the supernatant, the material was incubated at 4° C. for 2 hours with agitation, and immunoprecipitation was carried out. Monoclonal antibodies against polypeptide A used in immunoprecipitation were two of the 12 obtained in Working Example 3 which had low non-specific reactivity (monoclone numbers 114-1F2 and 114-2F2 [Assignment No. FERM BP-4743]). Next, Sepharose 4B coupled with monoclonal antibodies subjected to immunoprecipitation were precipitated by centrifugation, washed three times with a washing solution (0.01 M Tris-HCl buffer, pH 8 containing 1% Triton X-100, 1% bovine hemoglobin and 0.14 M NaCl), and lastly, washed with 0.05 M Tris-HCl buffer, pH 6.8. A sample buffer for SDS polyacrylamide electrophoresis was added to washed Sepharose-4B coupled with a monoclonal antibody, boiled 5 minutes at 100° C., and SDS polyacrylamide electrophoresis was carried out. The electrophoresed gel was layered with X-ray film (Kodak XR), 1 week autoradiography was then carried out at −70° C., and the developed X-ray films were traced by a densitometer to measure signal intensity. With each of the anti-MT-MMP monoclonal antibodies used (monoclone numbers 114-1F2 and 114-2F2), the immunoprecipitate contained a 63 kDa protein. In cells transfected with a pSG5 vector alone not containing an MT-MMP gene as a control, anti-MTMMP monoclonal antibodies (monoclone numbers 114-1F2 and 114-2F2) did not precipitate a 63 kDa protein. The 63 kDa molecular weight of the protein detected by immunoprecipitation nearly matched a molecular weight of 65.78 kDa calculated from the amino acid sequence denoted by SEQ ID NO:1. In addition, a variant MT-MMP expression plasmid was constructed in which amino acids from position 13 to position 101 were deleted from the amino acid sequence denoted by SEQ ID NO:1, HT1080 cells was transfected with said variant as stated above, and immunoprecipitation was carried out. With HT1080 cells to which the variant MT-MMP gene was introduced, a 63 kDa protein was not detected, and a 55 kDa protein was detected. This molecular weight matched a molecular weight predicted from the introduced deletion.

EXPERIMENTAL EXAMPLE (a) Activation of proMMP-2 by MT-MMP Expression

Recombinant pSG5 carrying a cloned MT-MMP gene, constructed in Working Example 4, and a pSG5 vector alone, serving as a control, similarly transfected into HT1080 cells by the calcium phosphate method mentioned in Working Example 4, or into mouse embryonic fibroblasts NIH3T3. However, a regular fresh culture medium was used in lieu of the fresh culture medium containing $^{35}$S-methionine. Both the HT1080 cells and the NIH3T3 cells secreted proMMP-2 and proMMP-9 (corresponding respectively to the 66 kDa and 97.4 kDa bands in FIG. 6), and in cells transfected with an MT-MMP gene, MT-MMP expression was confirmed by immunoprecipitation experiments (See Working Example 4).

The transfectants obtained were cultured for 24 hours in a serum free medium and the recovered culture supernatant was supplied for zymography. The culture supernatant was mixed with an SDS polyacrylamide electrophoresis buffer (non-reducing condition) and left at 4° C. overnight. Electrophoresis was then performed at 4° C., with a 20 mA current, using a 10% polyacrylamide gel containing 1 mg/ml casein. After electrophoresis, the gel was washed with a gelatinase-buffer (Tris-HCl buffer, pH 7.6 containing 5 mM $CaCl_2$ and 1 $\mu$M $ZnSO_4$) containing 2.5% Triton X-100 with gentle agitation for 15 minutes, and this operation was repeated twice. Next, the gel was immersed in a gelatinase-buffer containing 1% Triton X-100 and stood at 37° C. overnight. The buffer was discarded and the gel was stained for 1 hour with 0.02% Coomassie Brilliant Blue-R (dissolved in 50% methanol/10% acetic acid) and destained by immersion in a destaining solution (5% methanol, 7.5% acetic acid).

As shown in FIG. 6, MT-MMP gene-transfected HT1080 cells produced new 64 kDa and 62 kDa bands, confirming proMMP-2 activation. This active-form MMP-2 exhibited the same molecular weight as an active-form MMP-2 molecule induced by treatment of cells with 100 $\mu$g/ml of concanavalin A and reacted specifically against anti-MMP-2 monoclonal antibodies. This activation was not observed in a control transfected with a vector alone. Likewise, proMMP-9 showed no change in molecular weight and no activation similar to that observed in control cells. Such activation of proMMP-2 depending on MT-MMP expression was also observed in MT-MMP gene-transfected NIH3T3 cells.

(b) Activation of ProMMP-2 by MT-MMP Expression Cell Membrane Fraction

In a manner similar to that noted in the above section (a), African green monkey kidney-derived COS-1 cells were transfected with recombinant pSG5 containing cloned MT-MMP gene, or with control pSG5 vector alone by a calcium phosphate method. A cell membrane fraction was then prepared from the obtained transfectant according to the method of Strongin et al. (J. Biol. Chem., 268:14033–14039, 1993).

The transfectant was washed with PBS, and cells were harvested by centrifugation and suspended in a 25 mM Tris-HCl buffer, pH 7.4 containing 8.5% sucrose, 50 mM NaCl, 10 mM Nethylmaleimide, 10 $\mu$g/ml aprotinin, 1 $\mu$g/ml pepstatin A, 1 $\mu$g/ml leupeptin and 1 mM phenylmethylsulfonyl fluoride. The cell suspension was homogenized in a Dounce homogenizer, and the homogenate was centrifuged (3000× g, 10 min., 4° C.). The resulting supernatant was ultracentrifuged (100,000× g, 2 hours) and the precipitate was suspended in a 25mM TrisHCl buffer, pH 7.4 containing 50 mM NaCl, 10 mM N-ethylmaleimide, 10 $\mu$g/ml aprotinin, 1 $\mu$g/ml pepstatin A, 1 $\mu$g/ml leupeptin and 1 mM phenylmethylsulfonyl fluoride. This suspension was fractionated by discontinuous sucrose density gradient centrifugation (20, 30, 50, 60% sucrose solutions; 100,000× g; 2 hours; 4° C.), and bands of cell membrane fractions appeared were recovered. These fractions were precipitated again by ultracentrifugation (100,000× g, 2 hours), suspended in 25mM HEPES/KOH buffer, pH 7.5 containing 0.1mM $CaCl_2$ and 0.25% Triton X-100, and adjusted to a final protein concentration of 1-2 mg/ml. This suspension was ultracentrifuged (100,000× g, 1.5 hours, 4° C.) to remove insoluble residue, and the supernatant obtained was taken as a cell membrane fraction.

Cell membrane fractions (protein content 20 $\mu$g) respectively prepared from untreated COS-1 cells or from COS-1 cells transfected with pSG5 vector alone or pSG5 vector with an MT-MMP gene were incubated with HT1080 cell culture supernatant at 37° C. for 2 hours. Using these samples, the zymography noted in the above section (a) was performed.

In the results, new 64 kDa and 62 kDa bands appeared and the activation of proMMP-2 present in HT1080 cell culture supernatant was observed only when cell membrane fractions derived from MT-MMP gene-transfected COS-1 cells were used (see FIG. 7), and the activation of proMMP-2 was inhibited by the addition of recombinant (r) human TIMP-2. These results exhibited the activation of proMMP-2 by MT-MMP expressed on a cell membrane.

(c) Stimulation of cellular invasion in vitro due to MT-MMP expression

Invasion of cells was assayed by modified Boyden Chamber method (Cancer Res., 47:3239–3245, 1987), and operations were carried out in accordance with the manufacture's instructions for a Biocoat Matrigel Invasion Chamber (Becton Dickinson).

In a manner similar to that noted in the foregoing section (a), HT1080 cells or NIH3T3 cells were transfected with recombinant pSG5 carrying a cloned MT-MMP gene, or a control pSG5 vector alone, by a calcium phosphate method, and each of these host cells secreted proMMP-2. The resulting transfectants were then suspended in DMEM medium containing 0.1% BSA, and 2×10$^5$ cells were seeded onto an uncoated filter (pore size 8 $\mu$m) or a preswelled Matrigel Coat filter in a Biocoat Matrigel Invasion Chambers. After 24 hours incubation in a $CO_2$ incubator at 37° C., the filters were fixed by 10 seconds immersion in methanol. The filters were then stained by hematoxylin for 3 minutes, washed, and stained by eosin for 10 seconds, and the number of cells invaded the bottom surface of the filters were counted under a light microscope (at a magnification of ×400).

In the MT-MMP gene-transfected HT1080 cells and NIH3T3 cells, more than twice as many invading cells were seen compared to cells transfected with the control vector alone (See FIG. 8 Matrigel). Specifically, MT-MMP expression was seen to stimulate cellular invasion. Furthermore, the addition of 10 $\mu$g/ml of r-human TIMP-2 to this assay system clearly suppressed cellular invasion (see FIG. 8 Matrigel+r-human TIMP-2).

BRIEF DESCRIPTION OF THE FIGURES

FIGS. 2A, 2B, 2C, 2D, 2E, 2F, 2G and 2H are figures comparing sequential homology between the amino acid sequences of MT-MMPn SEQ ID NO:1 and those of the known MMP family (MMP1 (SEQ ID NO:12), MMP-2 (SEQ ID NO:17), MMP-3 (SEQ ID NO:15), MMP-7 (SEQ ID NO:18), MMP-8 (SEQ ID NO:13), MMP-9 (SEQ ID NO:16), MMP-10 and MMP-11) Letters in each figure indicate respective amino acids; A corresponding to Ala, C to Cys, D to Asp, E to Glu, F to Phe, G to Gly, H to His, I to Ile, K to Lys, L to Leu, M to Met, N to Asn, P to Pro, Q to Gln, R to Arg, S to Ser, T to Thr, V to Val, W to Trp and Y to Tyr. FIGS. 2A through 2H are an integral unit and comprise a single figure.

SEQUENCE LISTING

Figure 1:
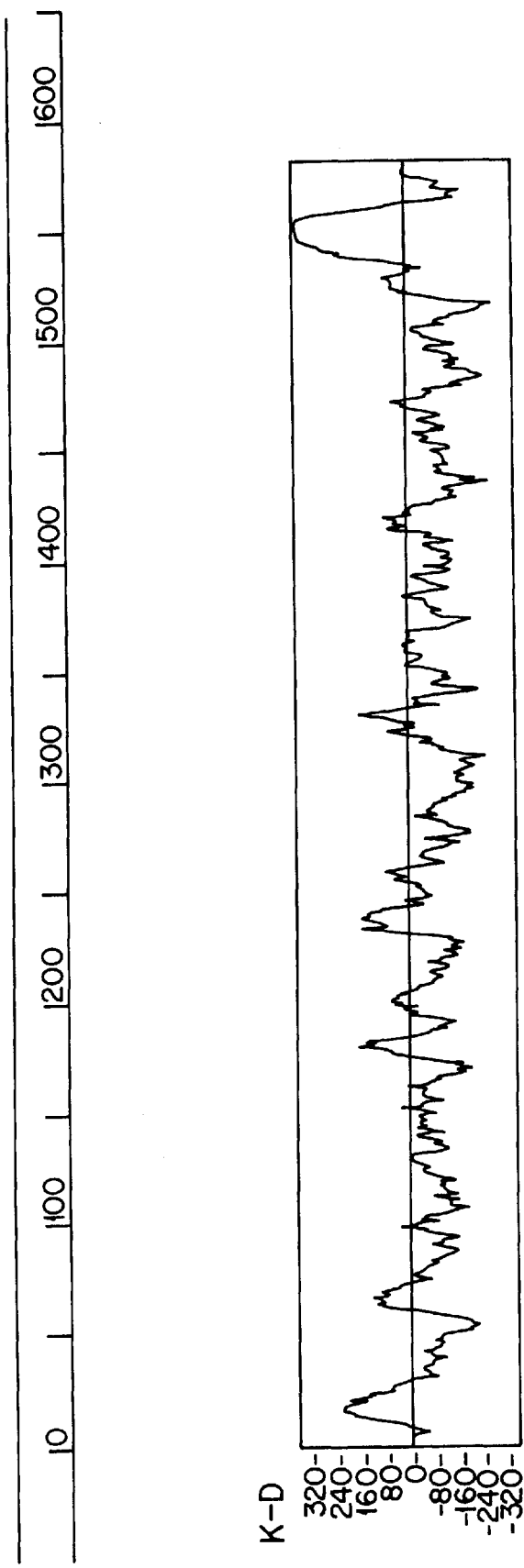
FIG. 1 shows hydrophilic and hydrophobic distribution diagrams for the amino acid sequence of MT-MMP, according to the Kyte-Doolittle method.
Figure 3:
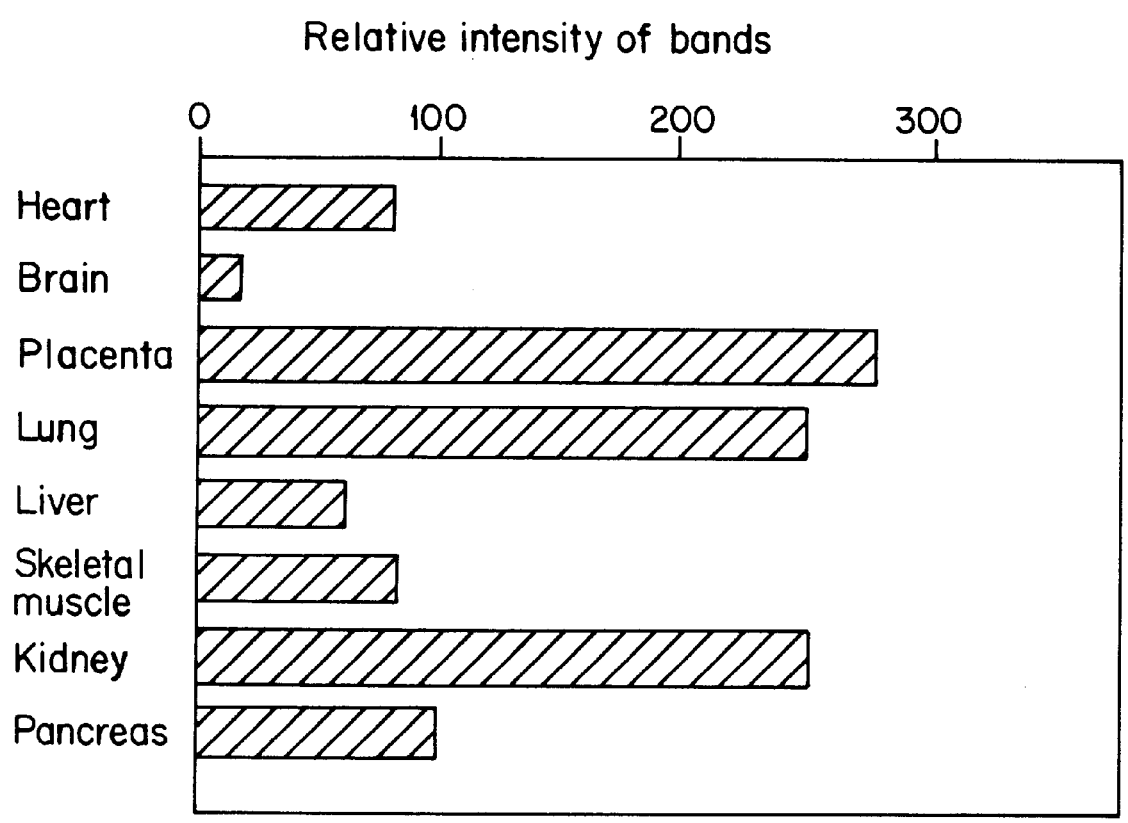
FIG. 3 shows a relative expression of MT-MMP mRNA in various human tissues, according to Northern blot analysis.
Figure 4:
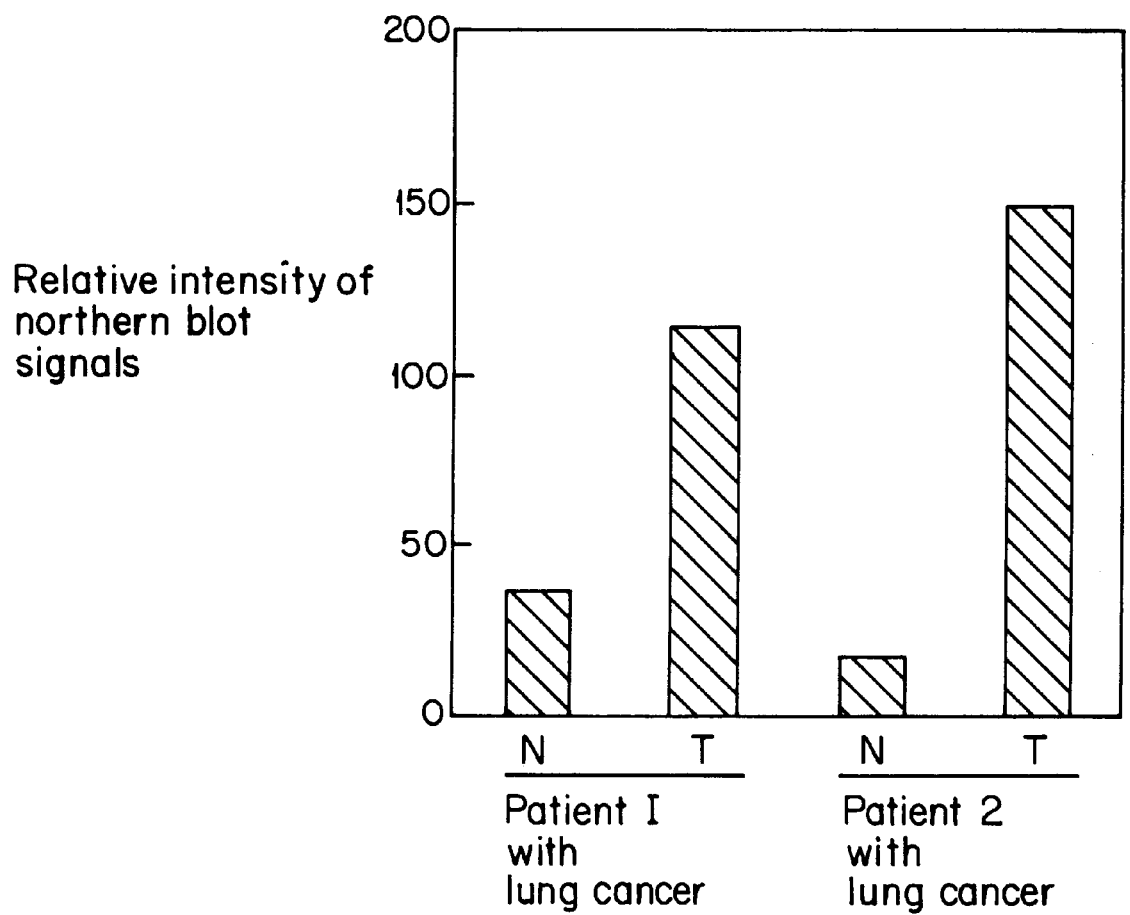
FIG. 4 shows a relative expression of MT-MMP mRNA in a normal tissue and a tumour tissue of two samples of human lung squamous cell carcinoma, according to Northern blot analysis.
Figure 5:
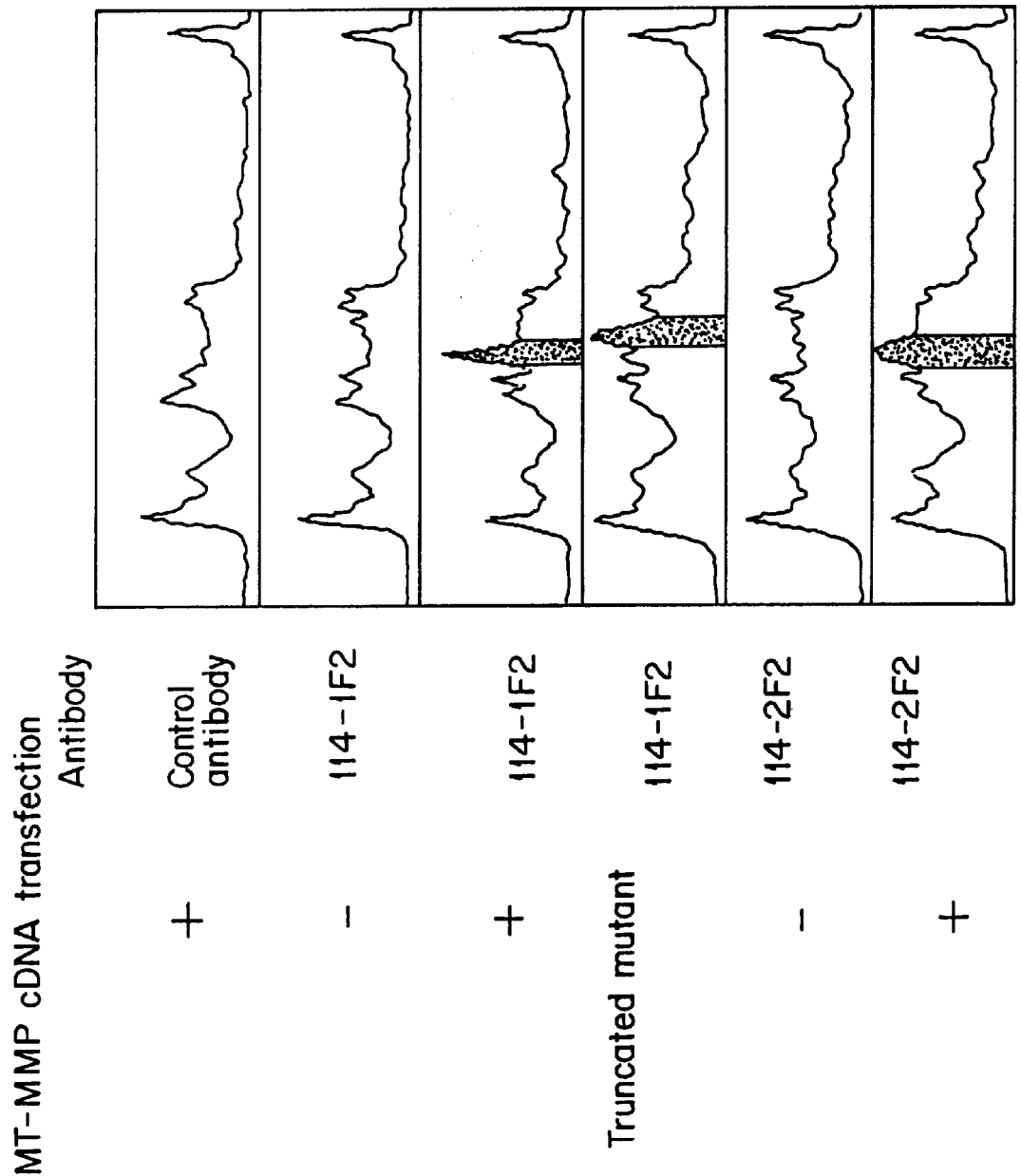
FIG. 5 shows results for detection, by immunoprecipitation, of MT-MMP proteins expressed in HT1080 cells transfected with MT-MMP cDNA. The figure shows a scan by a densitometer, and the darkened areas indicate the location of MT-MMP immunoprecipitated by anti-MT-MMP monoclonal antibody.
Figure 6:
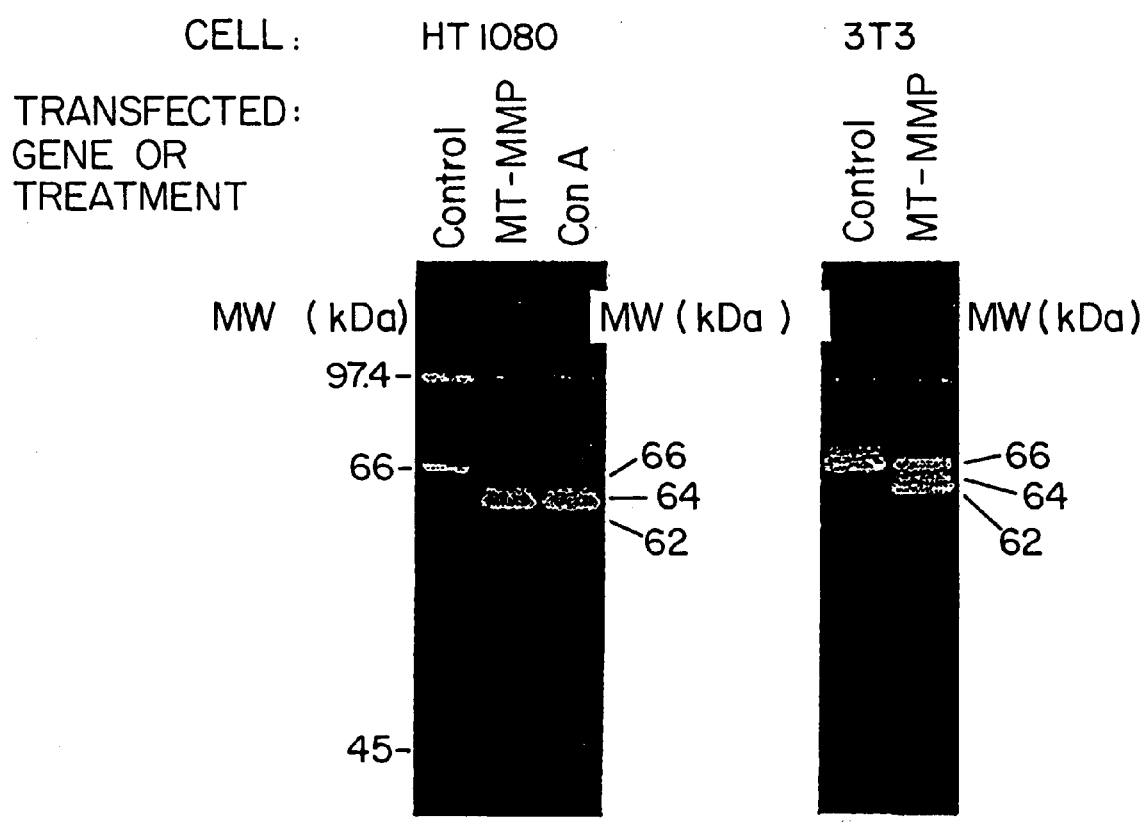
FIG. 6 shows an activation of proMMP-2 by expression of MT-MMP, according to zymography of culture supernatant from HT1080 and NIH3T3 cells transfected with MT-MMP cDNA.
Figure 7:
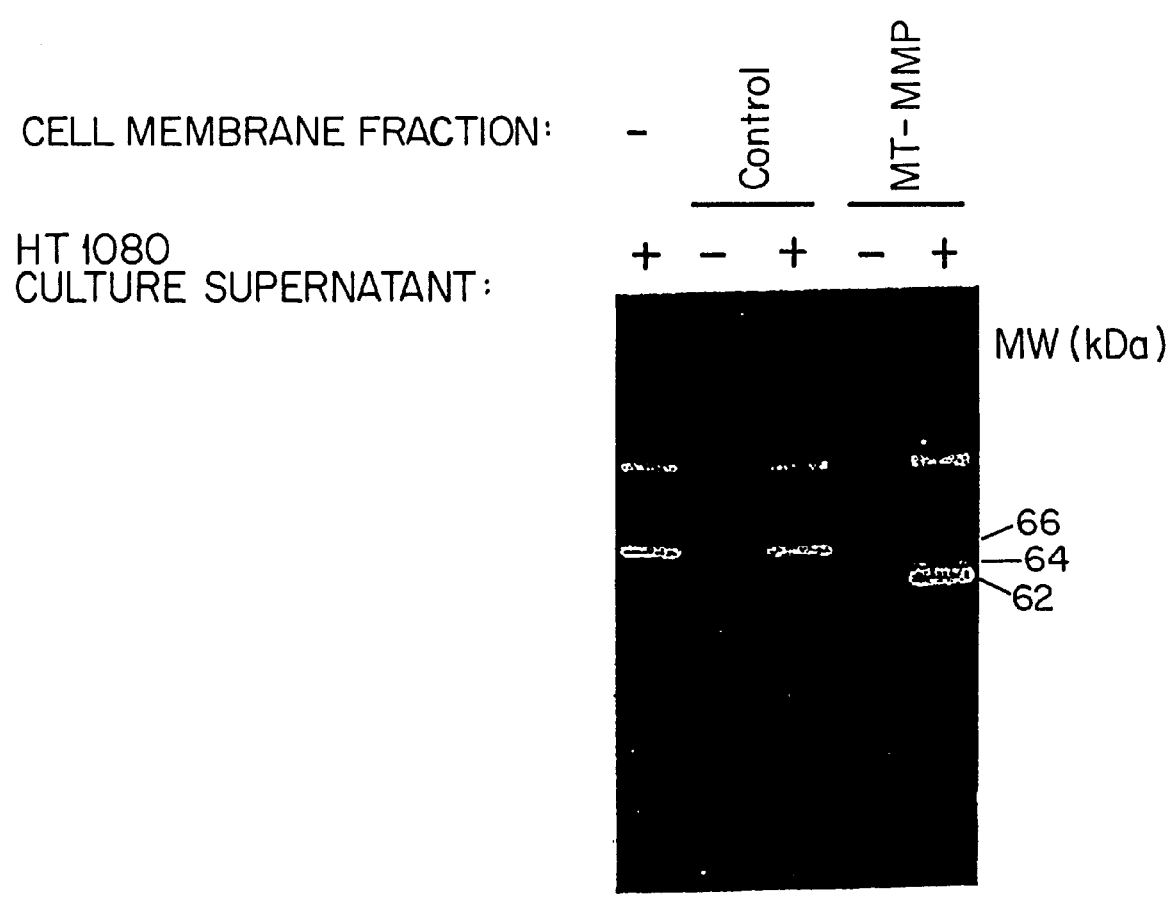
FIG. 7 shows an activation of proMMP-2 by a cell membrane fraction of COS-1 cells transfected with MT-MMP cDNA, according to zymography.
Figure 8:
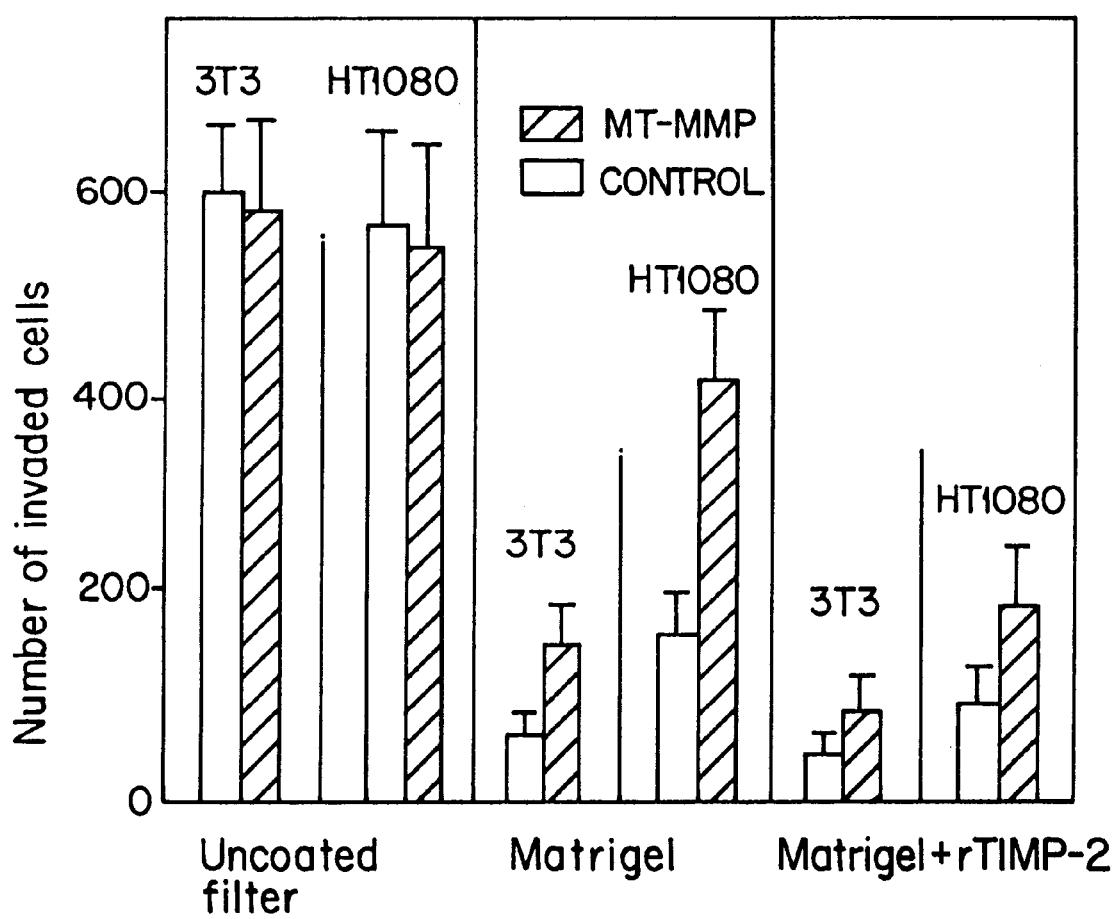
FIG. 8 shows a stimulation of the cellular invasion by expression of MT-MMP, according to a partially modified Boyden chamber method.

```
<160> NUMBER OF SEQ ID NOS: 19

<210> SEQ ID NO 1
<211> LENGTH: 582
<212> TYPE: PRT
<213> ORGANISM: Homo sapiens

<400> SEQUENCE: 1

Met Ser Pro Ala Pro Arg Pro Ser Arg Cys Leu Leu Leu Pro Leu Leu
 1               5                  10                  15

Thr Leu Gly Thr Ala Leu Ala Ser Leu Gly Ser Ala Gln Ser Ser Ser
             20                  25                  30

Phe Ser Pro Glu Ala Trp Leu Gln Gln Tyr Gly Tyr Leu Pro Pro Gly
         35                  40                  45

Asp Leu Arg Thr His Thr Gln Arg Ser Pro Gln Ser Leu Ser Ala Ala
     50                  55                  60

Ile Ala Ala Met Gln Lys Phe Tyr Gly Leu Gln Val Thr Gly Lys Ala
 65                  70                  75                  80

Asp Ala Asp Thr Met Lys Ala Met Arg Arg Pro Arg Cys Gly Val Pro
                 85                  90                  95

Asp Lys Phe Gly Ala Glu Ile Lys Ala Asn Val Arg Arg Lys Arg Tyr
            100                 105                 110

Ala Ile Gln Gly Leu Lys Trp Gln His Asn Glu Ile Thr Phe Cys Ile
        115                 120                 125

Gln Asn Tyr Thr Pro Lys Val Gly Glu Tyr Ala Thr Tyr Glu Ala Ile
    130                 135                 140

Arg Lys Ala Phe Arg Val Trp Glu Ser Ala Thr Pro Leu Arg Phe Arg
145                 150                 155                 160

Glu Val Pro Tyr Ala Tyr Ile Arg Glu Gly His Glu Lys Gln Ala Asp
                165                 170                 175

Ile Met Ile Phe Phe Ala Glu Gly Phe His Gly Asp Ser Thr Pro Phe
            180                 185                 190

Asp Gly Glu Gly Gly Phe Leu Ala His Ala Tyr Phe Pro Gly Pro Asn
        195                 200                 205

Ile Gly Gly Asp Thr His Phe Asp Ser Ala Glu Pro Trp Thr Val Arg
    210                 215                 220

Asn Glu Asp Leu Asn Gly Asn Asp Ile Phe Leu Val Ala Val His Glu
225                 230                 235                 240
```

-continued

```
Leu Gly His Ala Leu Gly Leu Glu His Ser Ser Asp Pro Ser Ala Ile
            245                 250                 255

Met Ala Pro Phe Tyr Gln Trp Met Asp Thr Glu Asn Phe Val Leu Pro
        260                 265                 270

Asp Asp Arg Arg Gly Ile Gln Gln Leu Tyr Gly Gly Glu Ser Gly
    275                 280                 285

Phe Pro Thr Lys Met Pro Pro Gln Pro Arg Thr Thr Ser Arg Pro Ser
290                 295                 300

Val Pro Asp Lys Pro Lys Asn Pro Thr Tyr Gly Pro Asn Ile Cys Asp
305                 310                 315                 320

Gly Asn Phe Asp Thr Val Ala Met Leu Arg Gly Glu Met Phe Val Phe
                325                 330                 335

Lys Lys Arg Trp Phe Trp Arg Val Arg Asn Asn Gln Val Met Asp Gly
            340                 345                 350

Tyr Pro Met Pro Ile Gly Gln Phe Trp Arg Gly Leu Pro Ala Ser Ile
        355                 360                 365

Asn Thr Ala Tyr Glu Arg Lys Asp Gly Lys Phe Val Phe Lys Gly
    370                 375                 380

Asp Lys His Trp Val Phe Asp Glu Ala Ser Leu Glu Pro Gly Tyr Pro
385                 390                 395                 400

Lys His Ile Lys Glu Leu Gly Arg Gly Leu Pro Thr Asp Lys Ile Asp
            405                 410                 415

Ala Ala Leu Phe Trp Met Pro Asn Gly Lys Thr Tyr Phe Phe Arg Gly
        420                 425                 430

Asn Lys Tyr Tyr Arg Phe Asn Glu Glu Leu Arg Ala Val Asp Ser Glu
    435                 440                 445

Tyr Pro Lys Asn Ile Lys Val Trp Glu Gly Ile Pro Glu Ser Pro Arg
    450                 455                 460

Gly Ser Phe Met Gly Ser Asp Glu Val Phe Thr Tyr Phe Tyr Lys Gly
465                 470                 475                 480

Asn Lys Tyr Trp Lys Phe Asn Asn Gln Lys Leu Lys Val Glu Pro Gly
            485                 490                 495

Tyr Pro Lys Ser Ala Leu Arg Asp Trp Met Gly Cys Pro Ser Gly Gly
        500                 505                 510

Arg Pro Asp Glu Gly Thr Glu Glu Glu Thr Glu Val Ile Ile Ile Glu
    515                 520                 525

Val Asp Glu Glu Gly Gly Ala Val Ser Ala Ala Val Val Leu
530                 535                 540

Pro Val Leu Leu Leu Leu Leu Val Leu Ala Val Gly Leu Ala Val Phe
545                 550                 555                 560

Phe Phe Arg Arg His Gly Thr Pro Arg Arg Leu Leu Tyr Cys Gln Arg
            565                 570                 575

Ser Leu Leu Asp Lys Val
            580

<210> SEQ ID NO 2
<211> LENGTH: 3403
<212> TYPE: DNA
<213> ORGANISM: Homo sapiens

<400> SEQUENCE: 2
agttcagtgc ctaccgaaga caaaggcgcc ccgagggagt ggcggtgcga ccccagggcg     60
tgggcccggc cgcggagcca cactgccggg ctgacccggt ggtctcggac catgtctccc    120
gccccaagac cctcccgttg tctcctgctc ccctgctca cgctcggcac cgcgctcgcc    180
```

-continued

```
tccctcggct cggcccaaag cagcagcttc agccccgaag cctggctaca gcaatatggc    240
tacctgcctc ccggggacct acgtacccac acacagcgct cacccagtc actctcagcg    300 gccatcgctg ccatgcagaa gttttacggc ttgcaagtaa caggcaaagc tgatgcagac    360
accatgaagg ccatgaggcg cccccgatgt ggtgttccag acaagtttgg ggctgagatc    420
aaggccaatg ttcgaaggaa cgctacgcc atccagggtc tcaaatggca acataatgaa    480
attactttct gcatccagaa ttaccccc aaggtgggcg agtatgccac atacgaggcc    540
attcgcaagg cgttccgcgt gtgggagagt gccacaccac tgcgcttccg cgaggtgccc    600
tatgcctaca tccgtgaggg ccatgagaag caggccgaca tcatgatctt ctttgccgag    660
ggcttccatg gcgacagcac gcccttcgat ggtgagggcg gcttcctggc ccatgcctac    720
ttcccagggc ccaacattgg aggagacacc cactttgact ctgccgagcc ttggactgtc    780
aggaatgagg atctgaatgg aaatgacatc ttcctggtgg ctgtgcacga gctgggccat    840 gccctgggc tcgagcattc cagtgacccc tcggccatca tggcacccct taccagtgg    900 atggacacgg agaattttgt gcttcccgat gatgaccgcc gggcatcca gcaactttat    960 gggggtgagt cagggttccc caccaagatg ccccctcaac ccaggactac ctcccggcct    1020
tctgttcctg ataaacccaa aaccccacc tatgggccca acatctgtga cgggaacttt    1080
gacaccgtgg ccatgctccg aggggagatg tttgtcttca agaagcgctg gttctggcgg    1140
gtgaggaata accaagtgat ggatggatac ccaatgccca ttggccagtt ctggcggggc    1200
ctgcctgcgt ccatcaacac tgcctacgag aggaaggatg gcaaattcgt cttcttcaaa    1260
ggagacaagc attgggtgtt tgatgaggcg tccctggaac ctggctaccc caagcacatt    1320
aaggagctgg gccgagggct gcctaccgac aagattgatg ctgctctctt ctggatgccc    1380 aatgaaaga cctacttctt ccgtggaaac aagtactacc gtttcaacga agagctcagg    1440
gcagtggata gcgagtaccc caagaacatc aaagtctggg aagggatccc tgagtctccc    1500
agagggtcat tcatgggcag cgatgaagtc ttcacttact tctacaaggg gaacaaatac    1560
tggaaattca caaccagaa gctgaaggta gaaccgggct accccaagtc agccctgagg    1620
gactggatgg gctgcccatc gggaggccgg ccggatgagg ggactgagga ggagacggag    1680
gtgatcatca ttgaggtgga cgaggagggc ggcggggcgg tgagcgcggc tgccgtggtg    1740
ctgcccgtgc tgctgctgct cctggtgctg gcggtgggcc ttgcagtctt cttcttcaga    1800
cgccatggga ccccaggcg actgctctac tgccagcgtt ccctgctgga caaggtctga    1860
cgcccatccg ccggcccgcc cactcctacc acaaggactt tgcctctgaa ggccagtggc    1920
agcaggtggt ggtgggtggg ctgctcccat cgtcccgagc cccctcccg cagcctcctt    1980 gcttctctct gtcccctggc tggcctcctt cacctgacc gcctccctcc ctcctgcccc    2040
ggcattgcat cttccctaga taggtcccct gagggctgag tgggagggcg cccctttcca    2100
gcctctgccc ctcaggggaa ccctgtagct ttgtgtctgt ccagccccat ctgaatgtgt    2160
tgggggctct gcacttgaag gcaggaccct cagacctcgc tggtaaaggt caaatgggt    2220 catctgctcc ttttccatcc cctgacatac cttaacctct gaactctgac ctcaggaggc    2280
tctggggaac tccagccctg aaagcccag gtgtacccaa ttggcagcct ctcactactc    2340
tttctggcta aaaggaatct aatcttgttg agggtagaga ccctgagaca gtgtgagggg    2400
gtggggactg ccaagccacc ctaagacctt gggaggaaaa ctcagagagg gtcttcgttg    2460
ctcagtcagt caagttcctc ggagatcttc ctctgcctca cctacccag ggaacttcca    2520
```

```
aggaaggagc ctgagccact ggggactaag tgggcagaag aaaccttgg cagccctgtg    2580 cctctcgaat gttagccttg gatggggctt tcacagttag aagagctgaa accaggggtg    2640
cagctgtcag gtagggtggg gccggtggga gaggcccggg tcagagccct gggggtgagc    2700
cttaaggcca cagagaaaga accttgccca aactcaggca gctgggctg aggcccaaag    2760 gcagaacagc cagaggggc aggaggggac caaaaaggaa aatgaggacg tgcagcagca    2820
ttggaaggct ggggcccggc agccaggtta aagctaacag ggggccatca gggtgggctt    2880
gtggagctct caggaagggc cctgaggaag gcacacttgc tcctgttggt ccctgtcctt    2940
gctgcccagg cagggtggag gggaagggta gggcagccag agaaaggagc agagaaggca    3000
cacaaacgag gaatgagggg cttcacgaga ggccacaggg cctggctggc cacgctgtcc    3060
cggcctgctc accatctcag tgagggacag gagctggggc tgcttaggct gggtccacgc    3120
ttccctggtg ccagcacccc tcaagcctgt ctcaccagtg gcctgccctc tcgctccccc    3180
acccagccca cccattgaag tctccttggg tcccaaaggt gggcatggta ccgggacttt    3240
gggagagtga gacccagtgg aggagcaag aggagaggga tgtggggggg tgggcacgg    3300 gtagggaaa tggggtgaac ggtgctggca gttcggctag atttctgtct tgtttgtttt    3360
tttgttttgt ttaatgtata tttttattat aattattata tat                     3403
```

<210> SEQ ID NO 3
<211> LENGTH: 7
<212> TYPE: PRT
<213> ORGANISM: Unknown
<220> FEATURE:
<223> OTHER INFORMATION: Description of Unknown Organism: Highly
      conserved sequence fragments from MMP family

<400> SEQUENCE: 3

Pro Arg Cys Gly Val Pro Asp
  1               5

<210> SEQ ID NO 4
<211> LENGTH: 9
<212> TYPE: PRT
<213> ORGANISM: Unknown
<220> FEATURE:
<223> OTHER INFORMATION: Description of Unknown Organism: Highly
      conserved sequence fragments from MMP family

<400> SEQUENCE: 4

Gly Asp Ala His Phe Asp Asp Asp Glu
  1               5

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 5
ccmmgvtgys gvrwbccwga                                                 20

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 6
ytcrtsvtcr tcraartgrr hrtcy                                                    25

<210> SEQ ID NO 7
<211> LENGTH: 30
<212> TYPE: PRT
<213> ORGANISM: Homo sapiens

<400> SEQUENCE: 7

Gly Gly Gly Ala Ser Ala Ala Val Val Leu Pro Val Leu Leu
 1               5                  10                  15

Leu Leu Leu Val Leu Ala Val Gly Leu Ala Val Phe Phe Phe
             20                  25                  30

<210> SEQ ID NO 8
<211> LENGTH: 14
<212> TYPE: PRT
<213> ORGANISM: Homo sapiens

<400> SEQUENCE: 8

Arg Glu Val Pro Tyr Ala Tyr Ile Arg Glu Gly His Glu Lys
 1               5                  10

<210> SEQ ID NO 9
<211> LENGTH: 14
<212> TYPE: PRT
<213> ORGANISM: Homo sapiens

<400> SEQUENCE: 9

Asp Gly Asn Phe Asp Thr Val Ala Met Leu Arg Gly Glu Met
 1               5                  10

<210> SEQ ID NO 10
<211> LENGTH: 15
<212> TYPE: PRT
<213> ORGANISM: Homo sapiens

<400> SEQUENCE: 10

Pro Lys Ser Ala Leu Arg Asp Trp Met Gly Cys Pro Ser Gly Gly
 1               5                  10                  15

<210> SEQ ID NO 11
<211> LENGTH: 489
<212> TYPE: PRT
<213> ORGANISM: Unknown
<220> FEATURE:
<223> OTHER INFORMATION: X = UNKNOWN
<220> FEATURE:
<223> OTHER INFORMATION: Description of Unknown Organism: Known Member
      of Matrix Metalloproteinase Family

<400> SEQUENCE: 11

Met Ala Pro Ala Ala Trp Leu Arg Ser Ala Ala Arg Ala Leu Leu
 1               5                  10                  15

Pro Pro Met Leu Leu Leu Leu Gln Pro Pro Leu Leu Ala Arg
             20                  25                  30

Ala Leu Pro Pro Asp Val His His Leu His Ala Glu Arg Arg Gly Pro
             35                  40                  45

Gln Pro Trp His Ala Ala Leu Pro Ser Ser Pro Ala Pro Ala Pro Ala
     50                  55                  60

Thr Gln Glu Ala Pro Arg Pro Ala Ser Ser Leu Arg Pro Pro Arg Cys
65                   70                  75                  80

```
Gly Val Pro Asp Pro Ser Asp Gly Leu Ser Ala Arg Asn Arg Gln Lys
                85                  90                  95
Arg Phe Val Leu Ser Gly Gly Arg Trp Glu Lys Thr Asp Leu Thr Tyr
            100                 105                 110
Arg Ile Leu Arg Phe Pro Trp Gln Leu Val Gln Glu Gln Val Arg Gln
        115                 120                 125
Thr Met Ala Glu Ala Leu Lys Val Trp Ser Asp Val Thr Pro Leu Thr
    130                 135                 140
Phe Thr Glu Val His Glu Gly Arg Ala Asp Ile Met Ile Asp Phe Ala
145                 150                 155                 160
Arg Tyr Trp Asp Gly Asp Asp Leu Pro Phe Asp Gly Pro Gly Gly Ile
                165                 170                 175
Leu Ala His Ala Phe Phe Pro Lys Thr His Arg Glu Gly Asp Val His
            180                 185                 190
Phe Asp Tyr Asp Glu Thr Trp Thr Ile Gly Asp Asp Gln Gly Thr Asp
        195                 200                 205
Leu Leu Gln Val Ala Ala His Glu Phe Gly His Val Leu Gly Leu Gln
    210                 215                 220
His Thr Thr Ala Ala Lys Ala Leu Met Ser Ala Phe Tyr Thr Phe Arg
225                 230                 235                 240
Tyr Pro Leu Ser Leu Ser Pro Asp Asp Cys Arg Gly Val Gln His Leu
                245                 250                 255
Tyr Gly Gln Pro Trp Pro Thr Val Thr Ser Arg Thr Pro Ala Leu Gly
            260                 265                 270
Pro Gln Ala Gly Ile Asp Thr Asn Glu Ile Ala Pro Leu Glu Pro Asp
        275                 280                 285
Ala Pro Pro Asp Ala Cys Glu Ala Ser Phe Asp Ala Val Ser Thr Ile
    290                 295                 300
Arg Gly Glu Leu Phe Phe Lys Ala Gly Phe Val Trp Arg Leu Arg
305                 310                 315                 320
Gly Gly Gln Leu Gln Pro Gly Tyr Pro Ala Leu Ala Ser Arg His Trp
            325                 330                 335
Gln Gly Leu Pro Ser Pro Val Asp Ala Ala Phe Glu Asp Ala Gln Gly
        340                 345                 350
His Ile Trp Phe Phe Gln Gly Ala Gln Tyr Trp Val Tyr Asp Gly Glu
    355                 360                 365
Lys Pro Val Leu Gly Pro Ala Pro Leu Thr Glu Leu Gly Leu Val Arg
370                 375                 380
Phe Pro Val His Ala Ala Leu Val Trp Gly Pro Glu Lys Asn Lys Ile
385                 390                 395                 400
Tyr Phe Phe Arg Gly Arg Asp Tyr Trp Arg Phe His Pro Ser Thr Arg
                405                 410                 415
Arg Val Asp Ser Pro Val Pro Arg Arg Ala Thr Asp Trp Arg Gly Val
            420                 425                 430
Pro Ser Glu Ile Asp Ala Ala Phe Gln Asp Ala Asp Gly Tyr Ala Tyr
        435                 440                 445
Phe Leu Arg Gly Arg Leu Tyr Trp Lys Phe Asp Pro Val Lys Val Lys
    450                 455                 460
Ala Leu Glu Gly Phe Pro Arg Leu Val Gly Pro Asp Phe Phe Gly Cys
465                 470                 475                 480
Ala Glu Pro Ala Asn Thr Phe Leu Xaa
                485
```

<210> SEQ ID NO 12
<211> LENGTH: 469
<212> TYPE: PRT
<213> ORGANISM: Unknown
<220> FEATURE:
<223> OTHER INFORMATION: Description of Unknown Organism: Known Member of Matrix Metalloproteinase Family

<400> SEQUENCE: 12

```
Met His Ser Phe Pro Pro Leu Leu Leu Leu Phe Trp Gly Val Val
 1               5                  10                  15

Ser His Ser Phe Pro Ala Thr Leu Glu Thr Gln Glu Gln Asp Val Asp
                20                  25                  30

Leu Val Gln Lys Tyr Leu Glu Lys Tyr Tyr Asn Leu Lys Asn Asp Gly
            35                  40                  45

Arg Gln Val Glu Lys Arg Arg Asn Ser Gly Pro Val Val Glu Lys Leu
50                  55                  60

Lys Gln Met Gln Glu Phe Phe Gly Leu Lys Val Thr Gly Lys Pro Asp
65                  70                  75                  80

Ala Glu Thr Leu Lys Val Met Lys Gln Pro Arg Cys Gly Val Pro Asp
                85                  90                  95

Val Ala Gln Phe Val Leu Thr Glu Gly Asn Pro Arg Trp Glu Gln Thr
            100                 105                 110

His Leu Thr Tyr Arg Ile Glu Asn Tyr Thr Pro Asp Leu Pro Arg Ala
        115                 120                 125

Asp Val Asp His Ala Ile Glu Lys Ala Phe Gln Leu Trp Ser Asn Val
    130                 135                 140

Thr Pro Leu Thr Phe Thr Lys Val Ser Glu Gly Gln Ala Asp Ile Met
145                 150                 155                 160

Ile Ser Phe Val Arg Gly Asp His Arg Asp Asn Ser Pro Phe Asp Gly
                165                 170                 175

Pro Gly Gly Asn Leu Ala His Ala Phe Gln Pro Gly Pro Gly Ile Gly
            180                 185                 190

Gly Asp Ala His Phe Asp Glu Asp Glu Arg Trp Thr Asn Asn Phe Thr
        195                 200                 205

Glu Tyr Asn Leu His Arg Val Ala Ala His Glu Leu Gly His Ser Leu
    210                 215                 220

Gly Leu Ser His Ser Thr Asp Ile Gly Ala Leu Met Tyr Pro Ser Tyr
225                 230                 235                 240

Thr Phe Ser Gly Asp Val Gln Leu Ala Gln Asp Asp Ile Asp Gly Ile
                245                 250                 255

Gln Ala Ile Tyr Gly Arg Ser Gln Asn Pro Val Gln Pro Ile Gly Pro
            260                 265                 270

Gln Thr Pro Lys Ala Cys Asp Ser Lys Leu Thr Phe Asp Ala Ile Thr
        275                 280                 285

Thr Ile Arg Gly Glu Val Met Phe Phe Lys Asp Arg Phe Tyr Met Arg
    290                 295                 300

Thr Asn Pro Phe Tyr Pro Glu Val Glu Leu Asn Phe Thr Ser Val Phe
305                 310                 315                 320

Trp Pro Gln Leu Pro Asn Gly Leu Glu Ala Ala Tyr Glu Phe Ala Asp
                325                 330                 335

Arg Asp Glu Val Arg Phe Phe Lys Gly Asn Lys Tyr Trp Ala Val Gln
            340                 345                 350

Gly Gln Asn Val Leu His Gly Tyr Pro Lys Asp Ile Tyr Ser Ser Phe
        355                 360                 365
```

```
Gly Phe Pro Arg Thr Val Lys His Ile Asp Ala Ala Leu Ser Glu Glu
    370                 375                 380

Asn Thr Gly Lys Thr Tyr Phe Val Ala Asn Lys Tyr Trp Arg Tyr
385                 390                 395                 400

Asp Glu Tyr Lys Arg Ser Met Asp Pro Gly Tyr Pro Lys Met Ile Ala
                405                 410                 415

His Asp Phe Pro Gly Ile Gly His Lys Val Asp Ala Val Phe Met Lys
                420                 425                 430

Asp Gly Phe Phe Tyr Phe Phe His Gly Thr Arg Gln Tyr Lys Phe Asp
                435                 440                 445

Pro Lys Thr Lys Arg Ile Leu Thr Leu Gln Lys Ala Asn Ser Trp Phe
    450                 455                 460

Asn Cys Arg Lys Asn
465

<210> SEQ ID NO 13
<211> LENGTH: 468
<212> TYPE: PRT
<213> ORGANISM: Unknown
<220> FEATURE:
<223> OTHER INFORMATION: X = UNKNOWN
<220> FEATURE:
<223> OTHER INFORMATION: Description of Unknown Organism: Known Member
      of Matrix Metalloproteinase Family

<400> SEQUENCE: 13

Met Phe Ser Leu Lys Thr Leu Pro Phe Leu Leu Leu Leu His Val Gln
  1               5                  10                  15

Ile Ser Lys Ala Phe Pro Val Ser Ser Lys Glu Lys Asn Thr Lys Thr
                20                  25                  30

Val Gln Asp Tyr Leu Glu Lys Phe Tyr Gln Leu Pro Ser Asn Gln Tyr
            35                  40                  45

Gln Ser Thr Arg Lys Asn Gly Thr Asn Val Ile Val Glu Lys Leu Lys
        50                  55                  60

Glu Met Gln Arg Phe Phe Gly Leu Asn Val Thr Gly Lys Pro Asn Glu
 65                  70                  75                  80

Glu Thr Leu Asp Met Met Lys Lys Pro Arg Cys Gly Val Pro Asp Ser
                 85                  90                  95

Gly Gly Phe Met Leu Thr Pro Gly Asn Pro Lys Trp Glu Arg Thr Asn
                100                 105                 110

Leu Thr Tyr Arg Ile Arg Asn Tyr Thr Pro Gln Leu Ser Glu Ala Glu
            115                 120                 125

Val Glu Arg Ala Ile Lys Asp Ala Phe Glu Leu Trp Ser Val Ala Ser
        130                 135                 140

Pro Leu Ile Phe Thr Arg Ile Ser Gln Gly Glu Ala Asp Ile Asn Ile
145                 150                 155                 160

Ala Phe Tyr Gln Arg Asp His Gly Asp Asn Ser Pro Phe Asp Gly Pro
                165                 170                 175

Asn Gly Ile Leu Ala His Ala Phe Gln Pro Gly Gln Gly Ile Gly Gly
                180                 185                 190

Asp Ala His Phe Asp Ala Glu Glu Thr Trp Thr Asn Thr Ser Ala Asn
            195                 200                 205

Tyr Asn Leu Phe Leu Val Ala Ala His Glu Phe Gly His Ser Leu Gly
        210                 215                 220

Leu Ala His Ser Ser Asp Pro Gly Ala Leu Met Tyr Pro Asn Tyr Ala
225                 230                 235                 240
```

-continued

```
Phe Arg Glu Thr Ser Asn Tyr Ser Leu Pro Gln Asp Asp Ile Asp Gly
            245                 250                 255

Ile Gln Ala Ile Tyr Gly Leu Ser Ser Asn Pro Ile Gln Pro Thr Gly
            260                 265                 270

Pro Ser Thr Pro Lys Pro Cys Asp Pro Ser Leu Thr Phe Asp Ala Ile
            275                 280                 285

Thr Thr Leu Arg Gly Glu Ile Leu Phe Phe Lys Asp Arg Tyr Phe Trp
290                 295                 300

Arg Arg His Pro Gln Leu Gln Arg Val Glu Met Asn Phe Ile Ser Leu
305                 310                 315                 320

Phe Trp Pro Ser Leu Pro Thr Gly Ile Gln Ala Ala Tyr Glu Asp Phe
            325                 330                 335

Asp Arg Asp Leu Ile Phe Leu Phe Lys Gly Asn Gln Tyr Trp Ala Leu
            340                 345                 350

Ser Gly Tyr Asp Ile Leu Gln Gly Tyr Pro Lys Asp Ile Ser Asn Tyr
            355                 360                 365

Gly Phe Pro Ser Ser Val Gln Ala Ile Asp Ala Ala Val Phe Tyr Arg
            370                 375                 380

Ser Lys Thr Tyr Phe Phe Val Asn Asp Gln Phe Trp Arg Tyr Asp Asn
385                 390                 395                 400

Gln Arg Gln Phe Met Glu Pro Gly Tyr Pro Lys Ser Ile Ser Gly Ala
            405                 410                 415

Phe Pro Gly Ile Glu Ser Lys Val Asp Ala Val Phe Gln Gln Glu His
            420                 425                 430

Phe Phe His Val Phe Ser Gly Pro Arg Tyr Tyr Ala Phe Asp Leu Ile
            435                 440                 445

Ala Gln Arg Val Thr Arg Val Ala Arg Gly Asn Lys Trp Leu Asn Cys
450                 455                 460

Arg Tyr Gly Xaa
465
```

<210> SEQ ID NO 14
<211> LENGTH: 476
<212> TYPE: PRT
<213> ORGANISM: Unknown
<220> FEATURE:
<223> OTHER INFORMATION: Description of Unknown Organism: Known Member
      of Matrix Metalloproteinase Family

<400> SEQUENCE: 14

```
Met Met His Leu Ala Phe Leu Val Leu Leu Cys Leu Pro Val Cys Ser
1               5                   10                  15

Ala Tyr Pro Leu Ser Gly Ala Ala Lys Glu Glu Asp Ser Asn Lys Asp
            20                  25                  30

Leu Ala Gln Gln Tyr Leu Glu Lys Tyr Tyr Asn Leu Glu Lys Asp Val
            35                  40                  45

Lys Gln Phe Arg Arg Lys Asp Ser Asn Leu Ile Val Lys Lys Ile Gln
        50                  55                  60

Gly Met Gln Lys Phe Leu Gly Leu Glu Val Thr Gly Lys Leu Asp Thr
65                  70                  75                  80

Asp Thr Leu Glu Val Met Arg Lys Pro Arg Cys Gly Val Pro Asp Val
            85                  90                  95

Gly His Phe Ser Ser Phe Pro Gly Met Pro Lys Trp Arg Lys Thr His
            100                 105                 110

Leu Thr Tyr Arg Ile Val Asn Tyr Thr Pro Asp Leu Pro Arg Asp Ala
```

```
                    115                 120                 125
Val Asp Ser Ala Ile Glu Lys Ala Leu Lys Val Trp Glu Glu Val Thr
    130                 135                 140
Pro Leu Thr Phe Ser Arg Leu Tyr Glu Gly Ala Asp Ile Met Ile
145                 150                 155                 160
Ser Phe Ala Val Lys Glu His Gly Asp Phe Tyr Ser Phe Asp Gly Pro
                    165                 170                 175
Gly His Ser Leu Ala His Ala Tyr Pro Pro Gly Pro Gly Leu Tyr Gly
                    180                 185                 190
Asp Ile His Phe Asp Asp Asp Glu Lys Trp Thr Glu Asp Ala Ser Gly
                    195                 200                 205
Thr Asn Leu Phe Leu Val Ala Ala His Glu Leu Gly His Ser Leu Gly
    210                 215                 220
Leu Phe His Ser Ala Asn Thr Glu Ala Leu Met Tyr Pro Leu Tyr Asn
225                 230                 235                 240
Ser Phe Thr Glu Leu Ala Gln Phe Arg Leu Ser Gln Asp Asp Val Asn
                    245                 250                 255
Gly Ile Gln Ser Leu Tyr Gly Pro Pro Ala Ser Thr Glu Glu Pro
                    260                 265                 270
Leu Val Pro Thr Lys Ser Val Pro Ser Gly Ser Glu Met Pro Ala Lys
    275                 280                 285
Cys Asp Pro Ala Leu Ser Phe Asp Ala Ile Ser Thr Leu Arg Gly Glu
290                 295                 300
Tyr Leu Phe Phe Lys Asp Arg Tyr Phe Trp Arg Arg Ser His Trp Asn
305                 310                 315                 320
Pro Glu Pro Glu Phe His Leu Ile Ser Ala Phe Trp Pro Ser Leu Pro
                    325                 330                 335
Ser Tyr Leu Asp Ala Ala Tyr Glu Val Asn Ser Arg Asp Thr Val Phe
                    340                 345                 350
Ile Phe Lys Gly Asn Glu Phe Trp Ala Ile Arg Gly Asn Glu Val Gln
                    355                 360                 365
Ala Gly Tyr Pro Arg Gly Ile His Thr Leu Gly Phe Pro Pro Thr Ile
    370                 375                 380
Arg Lys Ile Asp Ala Ala Val Ser Asp Lys Glu Lys Lys Thr Tyr
385                 390                 395                 400
Phe Phe Ala Ala Asp Lys Tyr Trp Arg Phe Asp Glu Asn Ser Gln Ser
                    405                 410                 415
Met Glu Gln Gly Phe Pro Arg Leu Ile Ala Asp Asp Phe Pro Gly Val
                    420                 425                 430
Glu Pro Lys Val Asp Ala Val Leu Gln Ala Phe Gly Phe Phe Tyr Phe
                    435                 440                 445
Phe Ser Gly Ser Ser Gln Phe Glu Phe Asp Pro Asn Ala Arg Met Val
    450                 455                 460
Thr His Ile Leu Lys Ser Asn Ser Trp Leu His Cys
465                 470                 475

<210> SEQ ID NO 15
<211> LENGTH: 477
<212> TYPE: PRT
<213> ORGANISM: Unknown
<220> FEATURE:
<223> OTHER INFORMATION: Description of Unknown Organism: Known Member
      of Matrix Metalloproteinase Family

<400> SEQUENCE: 15
```

-continued

```
Met Lys Ser Leu Pro Ile Leu Leu Leu Cys Val Ala Val Cys Ser
 1               5                  10                  15

Ala Tyr Pro Leu Asp Gly Ala Arg Gly Glu Asp Thr Ser Met Asn
             20                  25                  30

Leu Val Gln Lys Tyr Leu Glu Asn Tyr Tyr Asp Leu Lys Lys Asp Val
             35                  40                  45

Lys Gln Phe Val Arg Arg Lys Asp Ser Gly Pro Val Val Lys Lys Ile
     50                  55                  60

Arg Glu Met Gln Lys Phe Leu Gly Leu Glu Val Thr Gly Lys Leu Asp
 65                  70                  75                  80

Ser Asp Thr Leu Glu Val Met Arg Lys Pro Arg Cys Gly Val Pro Asp
                 85                  90                  95

Val Gly His Phe Arg Thr Phe Pro Gly Ile Pro Lys Trp Arg Lys Thr
                100                 105                 110

His Leu Thr Tyr Arg Ile Val Asn Tyr Thr Pro Asp Leu Pro Lys Asp
                115                 120                 125

Ala Val Asp Ser Ala Val Glu Lys Ala Leu Lys Val Trp Glu Glu Val
        130                 135                 140

Thr Pro Leu Thr Phe Ser Arg Leu Tyr Glu Gly Glu Ala Asp Ile Met
145                 150                 155                 160

Ile Ser Phe Ala Val Arg Glu His Gly Asp Phe Tyr Pro Phe Asp Gly
                165                 170                 175

Pro Gly Asn Val Leu Ala His Ala Tyr Ala Pro Gly Pro Gly Ile Asn
                180                 185                 190

Gly Asp Ala His Phe Asp Asp Asp Glu Gln Trp Thr Lys Asp Thr Thr
        195                 200                 205

Gly Thr Asn Leu Phe Leu Val Ala Ala His Glu Ile Gly His Ser Leu
210                 215                 220

Gly Leu Phe His Ser Ala Asn Thr Glu Ala Leu Met Tyr Pro Leu Tyr
225                 230                 235                 240

His Ser Leu Thr Asp Leu Thr Arg Phe Arg Leu Ser Gln Asp Asp Ile
                245                 250                 255

Asn Gly Ile Gln Ser Leu Tyr Gly Pro Pro Asp Ser Pro Glu Thr
                260                 265                 270

Pro Leu Val Pro Thr Glu Pro Val Pro Glu Pro Gly Thr Pro Ala
    275                 280                 285

Asn Cys Asp Pro Ala Leu Ser Phe Asp Ala Val Ser Thr Leu Arg Gly
    290                 295                 300

Glu Ile Leu Ile Phe Lys Asp Arg His Phe Trp Arg Lys Ser Leu Arg
305                 310                 315                 320

Lys Leu Glu Pro Glu Leu His Leu Ile Ser Ser Phe Trp Pro Ser Leu
                325                 330                 335

Pro Ser Gly Val Asp Ala Ala Tyr Glu Val Thr Ser Lys Asp Leu Val
            340                 345                 350

Phe Ile Phe Lys Gly Asn Gln Phe Trp Ala Ile Arg Gly Asn Glu Val
                355                 360                 365

Arg Ala Gly Tyr Pro Arg Gly Ile His Thr Leu Gly Phe Pro Pro Thr
    370                 375                 380

Val Arg Lys Ile Asp Ala Ala Ile Ser Asp Lys Glu Lys Asn Lys Thr
385                 390                 395                 400

Tyr Phe Phe Val Glu Asp Lys Tyr Trp Arg Phe Asp Glu Lys Arg Asn
                405                 410                 415

Ser Met Glu Pro Gly Phe Pro Lys Gln Ile Ala Glu Asp Phe Pro Gly
```

```
                    420             425             430
Ile Asp Ser Lys Ile Asp Ala Val Phe Glu Glu Phe Gly Phe Phe Tyr
            435                 440                 445

Phe Phe Thr Gly Ser Ser Gln Leu Glu Phe Asp Pro Asn Ala Lys Lys
        450                 455                 460

Val Thr His Thr Leu Lys Ser Asn Ser Trp Leu Asn Cys
465                 470                 475
```

<210> SEQ ID NO 16
<211> LENGTH: 708
<212> TYPE: PRT
<213> ORGANISM: Unknown
<220> FEATURE:
<223> OTHER INFORMATION: X = UNKNOWN
<220> FEATURE:
<223> OTHER INFORMATION: Description of Unknown Organism: Known Member
      of Matrix Metalloproteinase Family

<400> SEQUENCE: 16

```
Met Ser Leu Trp Gln Pro Leu Val Leu Val Leu Leu Val Leu Gly Cys
 1               5                  10                  15

Cys Phe Ala Ala Pro Arg Gln Arg Gln Ser Thr Leu Val Leu Phe Pro
                20                  25                  30

Gly Asp Leu Arg Thr Asn Leu Thr Asp Arg Gln Leu Ala Glu Glu Tyr
            35                  40                  45

Leu Tyr Arg Tyr Gly Tyr Thr Arg Val Ala Glu Met Arg Gly Glu Ser
    50                  55                  60

Lys Ser Leu Gly Pro Ala Leu Leu Leu Gln Lys Gln Leu Ser Leu
65                  70                  75                  80

Pro Glu Thr Gly Glu Leu Asp Ser Ala Thr Leu Lys Ala Met Arg Thr
                85                  90                  95

Pro Arg Cys Gly Val Pro Asp Leu Gly Arg Phe Gln Thr Phe Glu Gly
                100                 105                 110

Asp Leu Lys Trp His His His Asn Ile Thr Tyr Trp Ile Gln Asn Tyr
            115                 120                 125

Ser Glu Asp Leu Pro Arg Ala Val Ile Asp Asp Ala Phe Ala Arg Ala
    130                 135                 140

Phe Ala Leu Trp Ser Ala Val Thr Pro Leu Thr Phe Thr Arg Val Tyr
145                 150                 155                 160

Ser Arg Asp Ala Asp Ile Val Ile Gln Phe Gly Val Ala Glu His Gly
                165                 170                 175

Asp Gly Tyr Pro Phe Asp Gly Lys Asp Gly Leu Leu Ala His Ala Phe
            180                 185                 190

Pro Pro Gly Pro Gly Ile Gln Gly Asp Ala His Phe Asp Asp Asp Glu
    195                 200                 205

Leu Trp Ser Leu Gly Lys Gly Val Val Val Pro Thr Arg Phe Gly Asn
    210                 215                 220

Ala Asp Gly Ala Ala Cys His Phe Pro Phe Ile Phe Glu Gly Arg Ser
225                 230                 235                 240

Tyr Ser Ala Cys Thr Thr Asp Gly Arg Ser Asp Gly Leu Pro Trp Cys
                245                 250                 255

Ser Thr Thr Ala Asn Tyr Asp Thr Asp Asp Arg Phe Gly Phe Cys Pro
            260                 265                 270

Ser Glu Arg Leu Tyr Thr Arg Asp Gly Asn Ala Asp Gly Lys Pro Cys
    275                 280                 285

Gln Phe Pro Phe Ile Phe Gln Gly Gln Ser Tyr Ser Ala Cys Thr Thr
```

-continued

```
            290                 295                 300
Asp Gly Arg Ser Asp Gly Tyr Arg Trp Cys Ala Thr Thr Ala Asn Tyr
305                 310                 315                 320

Asp Arg Asp Lys Leu Phe Gly Phe Cys Pro Thr Arg Ala Asp Ser Thr
                325                 330                 335

Val Met Gly Gly Asn Ser Ala Gly Glu Leu Cys Val Phe Pro Phe Thr
                340                 345                 350

Phe Leu Gly Lys Glu Tyr Ser Thr Cys Thr Ser Glu Gly Arg Gly Asp
                355                 360                 365

Gly Arg Leu Trp Cys Ala Thr Thr Ser Asn Phe Asp Ser Asp Lys Lys
370                 375                 380

Trp Gly Phe Cys Pro Asp Gln Gly Tyr Ser Leu Phe Leu Val Ala Ala
385                 390                 395                 400

His Glu Phe Gly His Ala Leu Gly Leu Asp His Ser Ser Val Pro Glu
                405                 410                 415

Ala Leu Met Tyr Pro Met Tyr Arg Phe Thr Glu Gly Pro Pro Leu His
                420                 425                 430

Lys Asp Asp Val Asn Gly Ile Arg His Leu Tyr Gly Pro Arg Pro Glu
                435                 440                 445

Pro Glu Pro Arg Pro Pro Thr Thr Thr Pro Gln Pro Thr Ala Pro
450                 455                 460

Pro Thr Val Cys Pro Thr Gly Pro Pro Thr Val His Pro Ser Glu Arg
465                 470                 475                 480

Pro Thr Ala Gly Pro Thr Gly Pro Pro Ser Ala Gly Pro Thr Gly Pro
                485                 490                 495

Pro Thr Ala Gly Pro Ser Thr Ala Thr Thr Val Pro Leu Ser Pro Val
                500                 505                 510

Asp Asp Ala Cys Asn Val Asn Ile Phe Asp Ala Ile Ala Glu Ile Gly
                515                 520                 525

Asn Gln Leu Tyr Leu Phe Lys Asp Gly Lys Tyr Trp Arg Phe Ser Glu
                530                 535                 540

Gly Arg Gly Ser Arg Pro Gln Gly Pro Phe Leu Ile Ala Asp Lys Trp
545                 550                 555                 560

Pro Ala Leu Pro Arg Lys Leu Asp Ser Val Phe Glu Glu Pro Leu Ser
                565                 570                 575

Lys Lys Leu Phe Phe Phe Ser Gly Arg Gln Val Trp Val Tyr Thr Gly
                580                 585                 590

Ala Ser Val Leu Gly Pro Arg Arg Leu Asp Lys Leu Gly Leu Gly Ala
                595                 600                 605

Asp Val Ala Gln Val Thr Gly Ala Leu Arg Ser Gly Arg Gly Lys Met
                610                 615                 620

Leu Leu Phe Ser Gly Arg Arg Leu Trp Arg Phe Asp Val Lys Ala Gln
625                 630                 635                 640

Met Val Asp Pro Arg Ser Ala Ser Glu Val Asp Arg Met Phe Pro Gly
                645                 650                 655

Val Pro Leu Asp Thr His Asp Val Phe Gln Tyr Arg Glu Lys Ala Tyr
                660                 665                 670

Phe Cys Gln Asp Arg Phe Tyr Trp Arg Val Ser Ser Arg Ser Glu Leu
                675                 680                 685

Asn Gln Val Asp Gln Val Gly Tyr Val Thr Tyr Asp Ile Leu Gln Cys
                690                 695                 700

Pro Glu Asp Xaa
705
```

```
<210> SEQ ID NO 17
<211> LENGTH: 631
<212> TYPE: PRT
<213> ORGANISM: Unknown
<220> FEATURE:
<223> OTHER INFORMATION: Description of Unknown Organism: Known Member
      of Matrix Metalloproteinase Family

<400> SEQUENCE: 17

Ala Pro Ser Pro Ile Ile Lys Phe Pro Gly Asp Val Ala Pro Lys Thr
 1               5                  10                  15

Asp Lys Glu Leu Ala Val Gln Tyr Leu Asn Thr Phe Tyr Gly Cys Pro
            20                  25                  30

Lys Glu Ser Cys Asn Leu Phe Val Leu Lys Asp Thr Leu Lys Lys Met
        35                  40                  45

Gln Lys Phe Phe Gly Leu Pro Gln Thr Gly Asp Leu Asp Gln Asn Thr
    50                  55                  60

Ile Glu Thr Met Arg Lys Pro Arg Cys Gly Asn Pro Asp Val Ala Asn
65                  70                  75                  80

Tyr Asn Phe Phe Pro Arg Lys Pro Lys Trp Asp Lys Asn Gln Ile Thr
                85                  90                  95

Tyr Arg Ile Ile Gly Tyr Thr Pro Asp Leu Asp Pro Glu Thr Val Asp
            100                 105                 110

Asp Ala Phe Ala Arg Ala Phe Gln Val Trp Ser Asp Val Thr Pro Leu
        115                 120                 125

Arg Phe Ser Arg Ile His Asp Gly Glu Ala Asp Ile Met Ile Asn Phe
    130                 135                 140

Gly Arg Trp Glu His Gly Asp Gly Tyr Pro Phe Asp Gly Lys Asp Gly
145                 150                 155                 160

Leu Leu Ala His Ala Phe Ala Pro Gly Thr Gly Val Gly Gly Asp Ser
                165                 170                 175

His Phe Asp Asp Asp Glu Leu Trp Thr Leu Gly Glu Gly Gln Val Val
            180                 185                 190

Arg Val Lys Tyr Gly Asn Ala Asp Gly Glu Tyr Cys Lys Phe Pro Phe
        195                 200                 205

Leu Phe Asn Gly Lys Glu Tyr Asn Ser Cys Thr Asp Thr Gly Arg Ser
    210                 215                 220

Asp Gly Phe Leu Trp Cys Ser Thr Thr Tyr Asn Phe Glu Lys Asp Gly
225                 230                 235                 240

Lys Tyr Gly Phe Cys Pro His Glu Ala Leu Phe Thr Met Gly Gly Asn
                245                 250                 255

Ala Glu Gly Gln Pro Cys Lys Phe Pro Phe Arg Phe Gln Gly Thr Ser
            260                 265                 270

Tyr Asp Ser Cys Thr Thr Glu Gly Arg Thr Asp Gly Tyr Arg Trp Cys
        275                 280                 285

Gly Thr Thr Glu Asp Tyr Asp Arg Asp Lys Lys Tyr Gly Phe Cys Pro
    290                 295                 300

Glu Thr Ala Met Ser Thr Val Gly Gly Asn Ser Glu Gly Ala Pro Cys
305                 310                 315                 320

Val Phe Pro Phe Thr Phe Leu Gly Asn Lys Tyr Glu Ser Cys Thr Ser
                325                 330                 335

Ala Gly Arg Ser Asp Gly Lys Met Trp Cys Ala Thr Thr Ala Asn Tyr
            340                 345                 350

Asp Asp Asp Arg Lys Trp Gly Phe Cys Pro Asp Gln Gly Tyr Ser Leu
```

-continued

```
                355                 360                 365
Phe Leu Val Ala Ala His Glu Phe Gly His Ala Met Gly Leu Glu His
    370                 375                 380

Ser Gln Asp Pro Gly Ala Leu Met Ala Pro Ile Tyr Thr Tyr Thr Lys
385                 390                 395                 400

Asn Phe Arg Leu Ser Gln Asp Asp Ile Lys Gly Ile Gln Glu Leu Tyr
                405                 410                 415

Gly Ala Ser Pro Asp Ile Asp Leu Gly Thr Gly Pro Thr Pro Thr Leu
            420                 425                 430

Gly Pro Val Thr Pro Glu Ile Cys Lys Gln Asp Ile Val Phe Asp Gly
            435                 440                 445

Ile Ala Gln Ile Arg Gly Glu Ile Phe Phe Phe Lys Asp Arg Phe Ile
450                 455                 460

Trp Arg Thr Val Thr Pro Arg Asp Lys Pro Met Gly Pro Leu Leu Val
465                 470                 475                 480

Ala Thr Phe Trp Pro Glu Leu Pro Glu Lys Ile Asp Ala Val Tyr Glu
                485                 490                 495

Ala Pro Gln Glu Glu Lys Ala Val Phe Phe Ala Gly Asn Glu Tyr Trp
            500                 505                 510

Ile Tyr Ser Ala Ser Thr Leu Glu Arg Gly Tyr Pro Lys Pro Leu Thr
            515                 520                 525

Ser Leu Gly Leu Pro Pro Asp Val Gln Arg Val Asp Ala Ala Phe Asn
530                 535                 540

Trp Ser Lys Asn Lys Lys Thr Tyr Ile Phe Ala Gly Asp Lys Phe Trp
545                 550                 555                 560

Arg Tyr Asn Glu Val Lys Lys Lys Met Asp Pro Gly Phe Pro Lys Leu
                565                 570                 575

Ile Ala Asp Ala Trp Asn Ala Ile Pro Asp Asn Leu Asp Ala Val Val
            580                 585                 590

Asp Leu Gln Gly Gly Gly His Ser Tyr Phe Phe Lys Gly Ala Tyr Tyr
            595                 600                 605

Leu Lys Leu Glu Asn Gln Ser Leu Lys Ser Val Lys Phe Gly Ser Ile
    610                 615                 620

Lys Ser Asp Trp Leu Gly Cys
625                 630

<210> SEQ ID NO 18
<211> LENGTH: 267
<212> TYPE: PRT
<213> ORGANISM: Unknown
<220> FEATURE:
<223> OTHER INFORMATION: Description of Unknown Organism: Known Member
      of Matrix Metalloproteinase Family

<400> SEQUENCE: 18

Met Arg Leu Thr Val Leu Cys Ala Val Cys Leu Leu Pro Gly Ser Leu
1               5                   10                  15

Ala Leu Pro Leu Pro Gln Glu Ala Gly Gly Met Ser Glu Leu Gln Trp
            20                  25                  30

Glu Gln Ala Gln Asp Tyr Leu Lys Arg Phe Tyr Leu Tyr Asp Ser Glu
        35                  40                  45

Thr Lys Asn Ala Asn Ser Leu Glu Ala Lys Leu Lys Glu Met Gln Lys
    50                  55                  60

Phe Phe Gly Leu Pro Ile Thr Gly Met Leu Asn Ser Arg Val Ile Glu
65                  70                  75                  80
```

Ile Met Gln Lys Pro Arg Cys Gly Val Pro Asp Val Ala Glu Tyr Ser
                85                  90                  95

Leu Phe Pro Asn Ser Pro Lys Trp Thr Ser Lys Val Thr Tyr Arg
            100                 105                 110

Ile Val Ser Tyr Thr Arg Asp Leu Pro His Ile Thr Val Asp Arg Leu
            115                 120                 125

Val Ser Lys Ala Leu Asn Met Trp Gly Lys Glu Ile Pro Leu His Phe
    130                 135                 140

Arg Lys Val Val Trp Gly Thr Ala Asp Ile Met Ile Gly Phe Ala Arg
145                 150                 155                 160

Gly Ala His Gly Asp Ser Tyr Pro Phe Asp Gly Pro Gly Asn Thr Leu
                165                 170                 175

Ala His Ala Phe Ala Pro Gly Thr Gly Leu Gly Gly Asp Ala His Phe
            180                 185                 190

Asp Glu Asp Glu Arg Trp Thr Asp Gly Ser Ser Leu Gly Ile Asn Phe
            195                 200                 205

Leu Tyr Ala Ala Thr His Glu Leu Gly His Ser Leu Gly Met Gly His
    210                 215                 220

Ser Ser Asp Pro Asn Ala Val Met Tyr Pro Thr Tyr Gly Asn Gly Asp
225                 230                 235                 240

Pro Gln Asn Phe Lys Leu Ser Gln Asp Asp Ile Lys Gly Ile Gln Lys
                245                 250                 255

Leu Tyr Gly Lys Arg Ser Asn Ser Arg Lys Lys
                260                 265

<210> SEQ ID NO 19
<211> LENGTH: 231
<212> TYPE: PRT
<213> ORGANISM: Unknown
<220> FEATURE:
<223> OTHER INFORMATION: Description of Unknown Organism: Known Member
      of Matrix Metalloproteinase Family

<400> SEQUENCE: 19

Met Pro Leu Leu Leu Leu Glu Tyr Leu Glu Lys Leu Met Gln Lys
  1               5                  10                  15

Phe Gly Leu Val Thr Gly Lys Leu Asp Thr Leu Met Arg Lys Pro Arg
                20                  25                  30

Cys Gly Val Pro Asp Val Gly Phe Phe Pro Gly Pro Lys Trp Thr Leu
            35                  40                  45

Thr Tyr Arg Ile Asn Tyr Thr Pro Asp Leu Pro Val Asp Ala Lys Ala
    50                  55                  60

Phe Val Trp Ser Val Thr Pro Leu Thr Phe Arg Val Glu Gly Ala Asp
65                  70                  75                  80

Ile Met Ile Phe Ala His Gly Asp Tyr Pro Phe Asp Gly Pro Gly Gly
                85                  90                  95

Leu Ala His Ala Phe Pro Gly Pro Gly Ile Gly Gly Asp Ala His Phe
            100                 105                 110

Asp Asp Glu Trp Thr Asn Leu Phe Leu Val Ala Ala His Glu Gly His
            115                 120                 125

Ser Leu Gly Leu His Ser Asp Pro Ala Leu Met Tyr Pro Thr Phe Phe
    130                 135                 140

Leu Ser Gln Asp Asp Ile Gly Ile Gln Leu Tyr Gly Pro Pro Thr Cys
145                 150                 155                 160

Asp Phe Asp Ala Ile Thr Arg Gly Glu Phe Phe Lys Asp Arg Trp Arg
                165                 170                 175

-continued

```
Leu Ser Phe Trp Pro Leu Pro Asp Ala Ala Tyr Glu Phe Phe Gly Asn
            180                 185                 190
Tyr Trp Gly Gly Tyr Pro Ile Leu Gly Pro Val Asp Ala Ala Lys Thr
        195                 200                 205
Tyr Phe Phe Lys Trp Arg Asp Met Pro Gly Pro Ile Phe Pro Gly Asp
    210                 215                 220
Ala Val Phe Phe Trp Leu Cys
225             230
```

What is claimed is:

1. An isolated native membrane-type matrix-metalloproteinase, comprising an amino acid sequence from amino acid numbers 160 to 173, 320 to 333, 498 to 512, and a continuous sequence of hydrophobic amino acids peculiar to membrane-binding proteins from amino acid number 533 to 562 in the C terminus domain shown in SEQ ID NO:1.

2. An isolated native membrane-type matrix-metalloproteinase according to claim 1, having a length of 582 amino acids.

3. An isolated native membrane-type matrix-metalloproteinase comprising an amino acid sequence from amino acid number 1 to 173, 320 to 333 and 498 to 512 and 563 to 582, and a continuous sequence of hydrophobic amino acids peculiar to membrane-binding proteins from amino acid number 533 to 562 in the C terminus domain shown in SEQ ID NO:1.

4. An isolated protein having the amino acid sequence shown in SEQ ID NO:1.

5. An isolated native membrane-type matrix-metalloproteinase having a length of 582 amino acids and encoded by the nucleotide sequence of SEQ ID NO:2 or a DNA which hybridizes thereto under stringent conditions, wherein said hybridization is carried out at 42° C. in the presence of 50% formamide with washing at 68° C. in the presence of 0.15 M NaCl.

* * * * *